United States Patent
McComb et al.

(10) Patent No.: US 9,854,093 B2
(45) Date of Patent: Dec. 26, 2017

(54) HOSPITALITY PRIVATE BRANCH EXCHANGE (PBX) SYSTEM WITH DYNAMIC RULES FOR COMPLEMENTING MOBILE PHONES OF CURRENTLY CHECKED IN GUESTS

(71) Applicants: Innacloud Technologies LLC, Worthington, OH (US); Guest Tek Interactive Entertainment Ltd., Calgary (CA)

(72) Inventors: Russell D. McComb, Delaware, OH (US); Christopher Abnett, Grove City, OH (US); Andrew T. MacMillan, Calgary (CA)

(73) Assignees: Innacloud Technologies LLC, Worthington, OH (US); Guest Tek Interactive Entertainment Ltd., Calgary (CA)

( * ) Notice: Subject to any disclaimer, the term of this patent is extended or adjusted under 35 U.S.C. 154(b) by 0 days.

(21) Appl. No.: 14/557,365

(22) Filed: Dec. 1, 2014

(65) Prior Publication Data
US 2015/0156616 A1     Jun. 4, 2015

Related U.S. Application Data

(60) Provisional application No. 61/910,858, filed on Dec. 2, 2013, provisional application No. 61/952,088, filed on Mar. 12, 2014.

(51) Int. Cl.
*H04M 3/42* (2006.01)
*H04M 3/51* (2006.01)
(Continued)

(52) U.S. Cl.
CPC ......... *H04M 3/5116* (2013.01); *A61B 5/0004* (2013.01); *A61B 5/0022* (2013.01);
(Continued)

(58) Field of Classification Search
None
See application file for complete search history.

(56) References Cited

U.S. PATENT DOCUMENTS

| 7,162,020 B1 * | 1/2007 | Forte | H04M 3/42263 379/201.01 |
| 2007/0050197 A1 * | 3/2007 | Efron | G06Q 10/02 705/26.1 |

(Continued)

OTHER PUBLICATIONS

Innacloud Technologies, "Hosted PBX Solutions for the Hospitality Industry", filename dated May 12, 2011 (2 pages).
(Continued)

*Primary Examiner* — Shantell L Heiber
(74) *Attorney, Agent, or Firm* — Baker & Hostetler LLP

(57) ABSTRACT

A PBX system complements the mobile phones of users. Custom incoming and outgoing call rules are dynamically activated for users when the users begin utilizing a facility having at least one phone number and a number of internal phones. A custom rule causes outgoing calls made from an internal phone used by a user to have a caller ID phone number of the user's personal mobile phone rather than the facility's phone number. Another custom rule causes incoming calls made to the facility's phone number that have a source caller ID phone number matching a phone number in the user's mobile phone address book to be automatically forwarded directly to an internal phone currently utilized by the user. The user may install an application on their mobile phone, and another custom rule causes incoming calls at the user's mobile phone to be twinned while the user is at the facility.

15 Claims, 11 Drawing Sheets

(51) Int. Cl.
*G06Q 50/12* (2012.01)
*H04W 4/16* (2009.01)
*A61B 5/00* (2006.01)
*G06F 17/30* (2006.01)
*H04M 7/00* (2006.01)

(52) U.S. Cl.
CPC ........ *A61B 5/747* (2013.01); *G06F 17/30477* (2013.01); *G06Q 50/12* (2013.01); *H04M 3/42068* (2013.01); *H04M 3/42323* (2013.01); *H04M 7/0024* (2013.01); *H04W 4/16* (2013.01)

(56) References Cited

U.S. PATENT DOCUMENTS

| | | | |
|---|---|---|---|
| 2010/0183134 A1* | 7/2010 | Vendrow | H04M 3/42348 379/201.06 |
| 2010/0190474 A1* | 7/2010 | Rajguru | H04W 12/08 455/412.1 |
| 2010/0329443 A1 | 12/2010 | Montaner Gutierrez et al. | |
| 2011/0103564 A1* | 5/2011 | Couse | H04M 1/2535 379/201.03 |
| 2011/0130168 A1* | 6/2011 | Vendrow | H04M 1/57 455/556.1 |

OTHER PUBLICATIONS

Things, "VoiceCloud SIP Trunking, Hosted PBX, Voicemail & ACD", downloaded on Sep. 10, 2013 from: http://thing5.com/wp-content/themes/thing5/pdf/Thing5%20VoiceCloud.pdf (2 pages).

Enhanced VOIP Communications Inc., "What is a Hosted PBX?", downloaded on Sep. 10, 2013 from: http://www.easyofficephone.com/resources/hosted-pbx (8 pages).

Wikipedia, "Enhanced 9-1-1", downloaded on Dec. 16, 2013 from http://en.wikipedia.org/wiki/Enhanced_911 (12 pages).

Wikipedia, "Next Generation 9-1-1", downloaded on Dec. 16, 2013 from http://en.wikipedia.org/wiki/Next_Generation_9-1-1 (6 pages).

* cited by examiner

100

Example active incoming call rules at hotel while user ID #33 checked in ⟵ 138a

| User ID | Source caller ID | Forwarded call? | Original destination | New Destination(s) | Notes |
|---|---|---|---|---|---|
| 33 | 740-555-0133 | No | Hotel main number | VIP desk (Ext. 1039) | The user is automatically connected to VIP desk when the user calls the hotel from their own mobile phone. |
| 33 | 740-555-0133 | Yes | Hotel main number | 1. User's room (look-up from PMS)<br><br>2. User's mobile phone (740-555-0133) | All calls that are forwarded to the hotel from the user's mobile phone are automatically twinned to both the user's room and the user's mobile phone. |
| 33 | 740-555-0101 | * | Hotel main number | 1. User's room (look-up from PMS)<br><br>2. User's mobile phone (740-555-0133) | All calls received from pre-defined phonebook numbers for the user (e.g., their friends, family, coworkers, etc.) are automatically twinned to both the user's room and the user's mobile phone. |
| 33 | 740-555-0199 | | | | |
| 33 | 516-555-0179 | | | | |
| 33 | 649-555-0155 | | | | |
| ⋮ | ⋮ | ⋮ | ⋮ | ⋮ | ⋮ |
| * | * | * | Hotel main number | Auto-attendant | Default rule - incoming calls that don't match any of the active custom user rules will automatically be forwarded to the auto-attendant. |

Columns: 400 User ID, 402 Source caller ID, 404 Forwarded call?, 406 Original destination, 408 New Destination(s), 410 Notes Rows: 420, 422, 424, 426

FIG. 4

Example active <u>outgoing call rules</u> at hotel while user ID #33 checked in

| User ID | Source room | Source caller ID | Notes |
|---|---|---|---|
| 33 | 1. User's room (look-up from PMS) | 740-555-0133 | All outgoing calls from the user's in-room phone will the phone number of the user's mobile phone for caller ID. |
| ⋮ | ⋮ | ⋮ | ⋮ |
| * | * | Hotel main number | Default outgoing call rule - outgoing calls that are not from guest rooms with specified caller IDs use the hotel's main phone number as the caller ID. |

HOSPITALITY PRIVATE BRANCH EXCHANGE (PBX) SYSTEM WITH DYNAMIC RULES FOR COMPLEMENTING MOBILE PHONES OF CURRENTLY CHECKED IN GUESTS

CROSS-REFERENCE TO RELATED APPLICATIONS

This application claims the benefit of priority of U.S. Provisional Patent Application No. 61/910,858 filed Dec. 2, 2013 and U.S. Provisional Patent Application No. 61/952,088 filed Mar. 12, 2014; both of these applications are incorporated herein by reference.

BACKGROUND OF THE INVENTION (1) Field of the Invention

The invention pertains generally to business phone systems, often referred to as private branch exchanges (PBXs). More specifically, the invention relates to a hospitality PBX system with dynamic user-based rules to better cooperate with the personal mobile phones of currently checked in guests.

(2) Description of the Related Art

Before the invention of the cell phone, private branch exchange (PBX) systems employing per-call billing were typically revenue generators for hotels. Take for example the situation where a guest without a cell phone is staying at a hotel and needs to make a phone call; the most convenient option is for the guest to use the phone provided in the guest's hotel room. To profit from this convenience, most hotels automatically charge for long distance calls made via the in-room phone, and some enterprising hotels charge for local calls in a similar manner. In-room phone charges typically show up as an itemized list along with the guest's folio at checkout, and calls may be charged on either a per-minute or per-usage basis.

Although many hotels currently charge for calls made by guests via in-room phones, hotel PBX systems are no longer the cash cows they used to be. In today's age of ubiquitous mobile phones, guests typically arrive with their own phone in pocket. The in-room phone is shunned by a guest equipped with a mobile phone except perhaps to call the front desk or to directly dial another guest room. Especially for heavy phone users, as long as there is sufficient cell phone signal coverage, guests almost always prefer to use their own mobile phone rather than the in-room phone for both incoming and outgoing calls. From the guest's point of view, there is often no advantage and several disadvantages with using the in-room phone rather the guest's personal mobile phone. As such, the legacy hotel PBX system is simply unable to compete with a guest's personal mobile phone.

Recognizing these trends along with the rise of popularity of mobile phones, some hotel insiders predicted that the in-room guest phone would simply disappear. The rational was as follows: if guests are making minimal use of the in-room phone because everyone nowadays has their own cell phone, why not save some money by not providing a phone in each room? Contrary to these predictions and despite low usage numbers, the in-room guest phone is still here for emergency preparedness. A guest without a functioning cell phone will expect there to be a working in-room phone in an emergency situation such as a fire. Recognizing that in-room guest phones act as emergency equipment, American and Canadian hotels are required to ensure that each guest room has a wired phone: in the U.S.A., the handset of the in-room phone may be cordless as long as the base station is wired; in Canada, the in-room phone is required to be wired right up to the handset.

As such, the current state of the art is that hotels generally incur costs to install and maintain a PBX system and an in-room phone in each guest room, but this equipment at best generates only small profit for the hotel and more typically generates losses because it is rarely utilized by guests.

BRIEF SUMMARY OF THE INVENTION

According to an exemplary embodiment of the invention, a hotel PBX system is disclosed that co-operates with and complements the mobile phones of the hotel's guests. When a guest checks in to a guest room, the PBX system automatically activates a number of custom call rules for the guest. One custom call rule causes outgoing calls made from the in-room phone in the guest's room to have a caller ID phone number of the guest's personal mobile phone. Another custom call rule causes incoming calls made to the hotel's main phone line that have a source caller ID phone number matching a phone number in the guest's mobile phone address book to be automatically forwarded directly to the guest's assigned MOM.

In an exemplary embodiment of the invention, the guest may install a predetermined application on their mobile phone that automatically detects when the guest is checked in to the hotel and activates a call twining function on the mobile phone. When activated, the call twinning function sends a notification to the hotel's PBX system when an incoming call comes in at the mobile device. The PBX system then causes the in-room phone of the guest's assigned room to ring and the caller ID information of the incoming call is displayed on the in-room phone as well. The guest may choose to answer the call at either of the mobile phone or the in-room guest phone. If the call is answered at the mobile phone then the application on the mobile phone sends a notification to the hotel PBX system and the in-room phone stops ringing. If the call is answered at the in-room guest phone then the hotel PBX notifies the application to forward the call from the mobile phone to the hotel PBX and the call is connected to the in-room phone at which it was answered.

In an exemplary embodiment of the invention, processing of real time events is done locally rather than in the cloud while still keeping non-real time events and redundancy in the cloud.

In an exemplary embodiment of the invention, rather than merely acting as an insurance policy for emergencies and accommodating the rare guest who lacks their own mobile phone, an advantage enabled by certain embodiments of the invention includes encouraging guests to make more frequent use of the hotel PBX system. Benefits may be obtained by guests such as better voice quality on calls via the in-room phone than is possible with a typical mobile phone, receiving calls at the guest's choice of the in-room phone or their mobile phone depending on the guest's location, and not avoiding the in-room phone for outgoing calls due to the caller ID of the in-room phone being unknown to the recipients of the outgoing calls. Guest satisfaction is increased and the hotel may monetize the increased in-room phone usage.

These and other advantages of the present invention will no doubt become apparent to those of ordinary skill in the art after reading the following detailed description of the preferred embodiment that is illustrated in the various figures and drawings.

BRIEF DESCRIPTION OF THE DRAWINGS

The invention will be described in greater detail with reference to the accompanying drawings which represent preferred embodiments thereof.

FIG. 4 shows example active incoming call rules stored at the onsite PBX server at the hotel while a guest having a certain user identifier is checked in to the hotel.

FIG. 5 shows example active outgoing call rules stored at the onsite PBX server at the hotel while a guest having a certain user identifier is checked in to the hotel.

DETAILED DESCRIPTION

Figure 1:
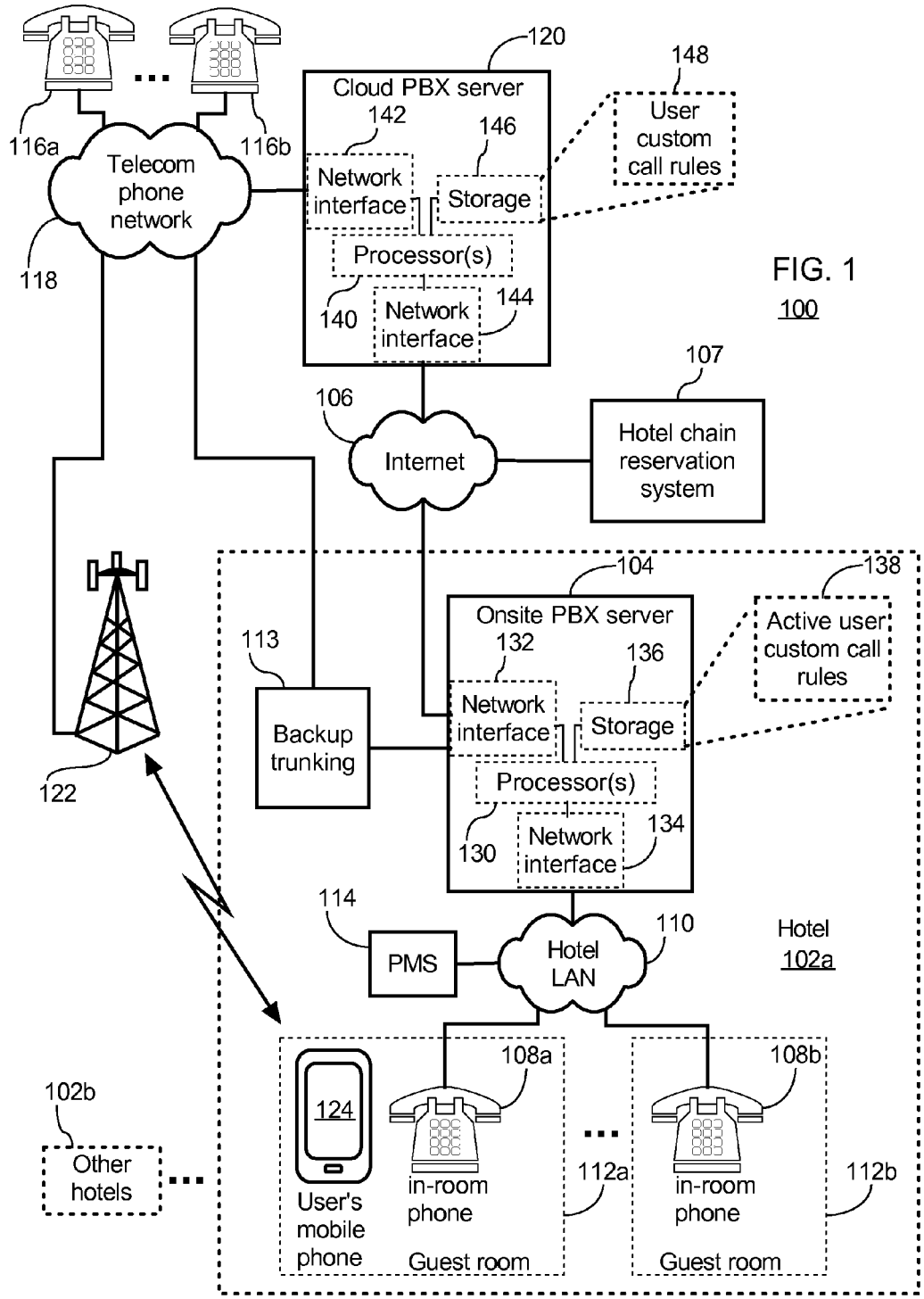
FIG. 1 shows a block diagram of a hybrid private branch exchange (PBX) system according to an exemplary embodiment of the invention.

FIG. 1 shows a hybrid private branch exchange (PBX) system 100 according to an exemplary embodiment of the invention. In this embodiment, the PBX system 100 is deployed to provide telephone services at a plurality of hotels 102. As shown in FIG. 1, a first hotel 102a includes an onsite PBX server 104 coupled to the Internet 106. The onsite PBX server 104 is also coupled to a plurality of in-room phones 108 via the hotel's local area network (LAN) 110. In this example, each of the in-room phones 108 is located in a different guest room 112, namely, a first in-room phone 108a is located in a first guest room 112a and a second in-room phone 108b is located in a second guest room 112b. The hotel 102a also includes a property management system (PMS) 114, which manages guest check-ins and check-outs along with room assignments.

The onsite PBX server 104 handles all local telephone calls (i.e., peer-to-peer) between phones 108 at the hotel property. As such, the data representing local calls between in-room phones 108 does not need to be routed via the Internet 106. For calls that are incoming from or outgoing to external phone numbers, represented in FIG. 1 as the external phones 116 shown coupled to telecom phone network 118, the onsite PBX server 104 works in tandem with a cloud PBX server 120 so that data for external calls is routed through the Internet 106. The cloud PBX server 120 also handles other non-real time tasks such as database storage, logging, and configuration, and licensing functionality, and some or all of these functions may be replicated locally on the onsite PBX server 104 for backup. In the event that either the hotel's 102a connection to the Internet 106 or the cloud PBX server 120 fails, backup trunking 113 is provided at the hotel to connect to the telecom phone network 118 such as via plain old telephone service (POTS) lines. Although only one hotel 102a is shown expanded in FIG. 1 so that the above described internal components are visible, the other hotels 102b may also include similar components.

The system 100 further includes a hotel chain reservation system 107 coupled to the Internet 104. The reservation system 107 may be a web server allowing guests and travel agents to reserve hotel rooms at any of the hotels 102. FIG. 1 also illustrates a cell phone tower 122 coupled to the telecom phone network 118, and, in the following examples, cell phone tower 122 is assumed to provide adequate cell phone coverage to a user's mobile phone 124 shown located within the first guest room 108a. Mobile phone 124 in this example is a personal mobile phone brought to the hotel by the current user of the first guest room 112a, i.e., the currently registered guest of the first guest room 112a.

In this embodiment, both the onsite PBX server 112 and the cloud PBX server 120 are implemented as computer servers including typical hardware such as processors, memory, and communications interfaces provided by a computer. For instance, the onsite PBX server 112 includes a one or more processors 130 coupled to network interfaces 132, 134 and a storage media 136. In this example, the first network interface 132 is a cable modem coupled to the Internet 104, the second network interface 134 is an Ethernet interface coupled to hotel LAN 110, and the storage media 136 is a combination of a hard drive and random access memory (RAM) storing, among other data and software, a set of active user custom call rules 138. Similarly, the cloud PBX server includes one or more processors 140 coupled to network interfaces 142, 144 and a storage media 146. In this example, the first network interface 142 is internet protocol (IP) based interface providing connectivity to the telecom phone network 118 (which may in fact be via the Internet 104), the second network interface 134 is a Ethernet interface coupled to a gigabit Ethernet connection within an cloud hosting provider providing connectivity to the Internet 104, and the storage media 146 is a combination of a hard drive and RAM storing, among other data and software, a set of user custom call rules 148.

In the example embodiment of FIG. 1, the processors 130, 140 of the onsite PBX server 112 and the cloud PBX server 120 execute various computer programs (i.e., computer executable instructions) loaded from non-transitory storage media 136, 146. The processors 130, 140 are configured via the computer programs to perform various functions as described in the following. In the following description, the plural form of the word "processors" is utilized as it is common for a central processing unit (CPU) of a computer server to have multiple processors (sometimes also referred to as cores); however, it is to be understood that a single processor may also be configured to perform the below-described functionality for each of the PBX servers 102, 120 in other implementations.

Figure 2:
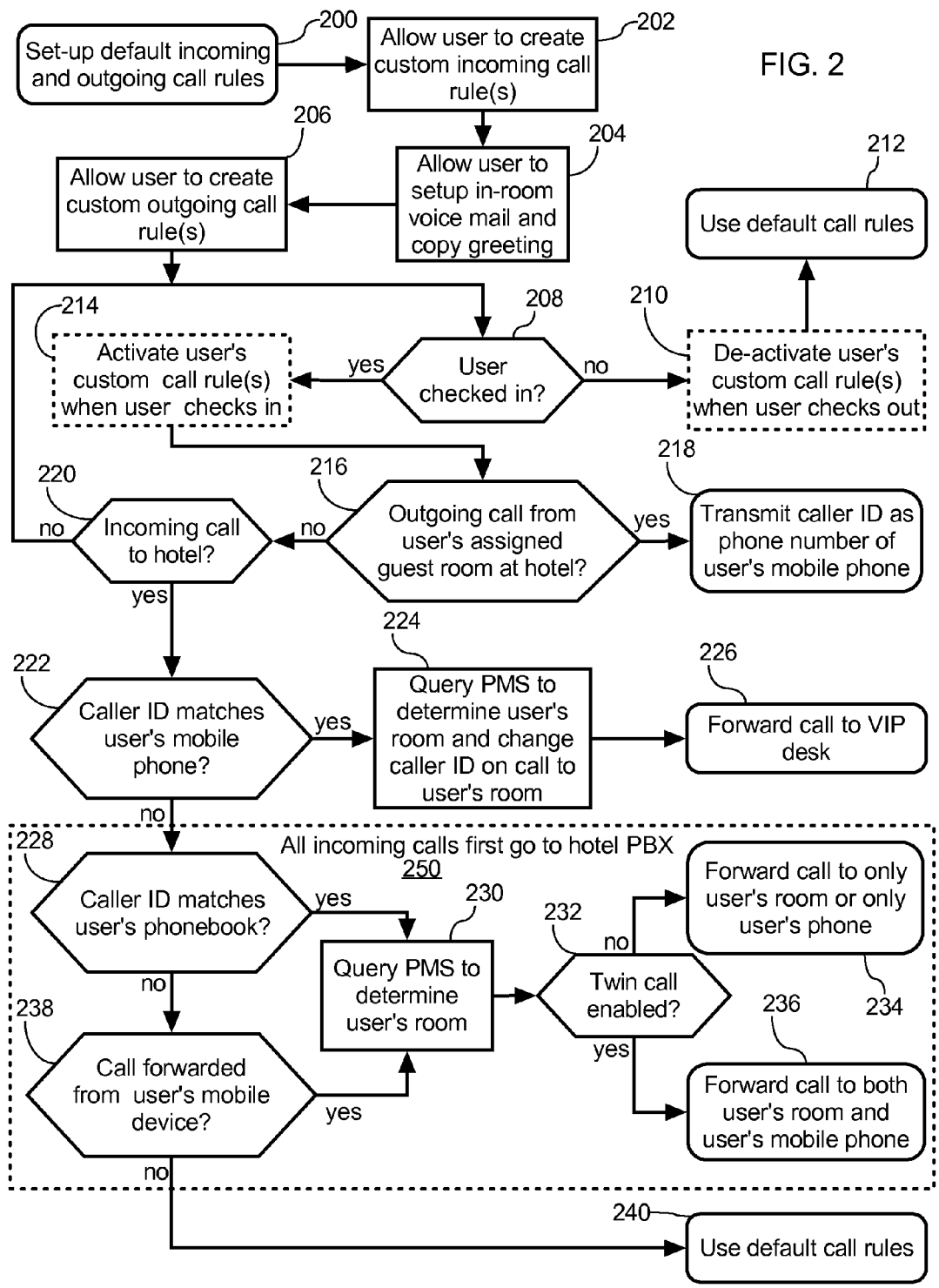
FIG. 2 shows a method of processing telephone calls in the hybrid PBX system of FIG. 1 according to an exemplary embodiment of the invention.

FIG. 2 shows a method of processing telephone calls in the hospitality PBX system 100 of FIG. 1 according to an exemplary embodiment of the invention. With reference to FIG. 1, some of the steps of FIG. 2 are performed by the processors 130, 140 of either the onsite PBX server 102 and/or the cloud PBX server 120, while other of the steps are performed by system administrators and users themselves. The steps of the flowchart are not restricted to the exact order shown, and, in other configurations, shown steps may be omitted or other intermediate steps added. In this embodiment, the system 100 operates as follows:

At step 200, default incoming and outgoing call rules are established at onsite PBX server 104 of the hotel 102a. In this embodiment, an administrator of the hotel 102a decides what will happen when an external phone 116 calls the main phone number of the hotel, for example, whether the incoming call should be directed to the hotel front desk or to an automated attendant. This default rule for incoming calls may be dependent upon the time of the day; for example, incoming calls during business hours may be directed to the front desk and incoming calls outside of business hours may be directed to an automated attendant.

Likewise, at step 200, the administrator also sets up a default outgoing call rule that indicates what the source caller ID of a call made from the hotel will show when a call is placed from the hotel to an external phone 116. A typical caller ID value will be the phone number of the hotel's main line. Optionally, each guest room 112 may have a unique phone number and the default caller ID value for a call placed from a particular guest room 112 will be the unique number of that particular guest room 112.

The default incoming and outgoing call rules set up at this step may be programmed into the onsite PBX server via a web interface accessible to hotel administrators or may be performed by a vender of the PBX system during installation after instruction from the hotel administrators. The settings for the default incoming and outgoing call rules are stored on the local storage media 136 within the onsite PBX server 104 and are also replicated and stored on the cloud storage 146 within the cloud PBX server 120. In this manner, should the onsite PBX server 104 lose its stored settings due to a fault, they may be retrieved from the cloud PBX server 120.

At step 202, the system 100 stores one or more custom incoming call rule(s). In this embodiment, some custom incoming call rules refer to rules that will direct an incoming call that is received at the main phone number of the hotel 102a to a custom destination that is different than the default destination as specified by the default rule. For example, if the default incoming call rule forwards all incoming calls to the front desk, a custom incoming call rule created at this step may instead forward incoming calls with a specific caller ID phone number to a different destination within the hotel 102a, i.e., calls from a guest's spouse's cell phone number will be forwarded to the in-room phone 108 of the particular guest room 112 where the guest is staying. In this way, the guest's spouse does not need to ask for a transfer at the front desk; likewise, front desk staff are saved time because they do not need to answer the incoming call.

Figure 3:
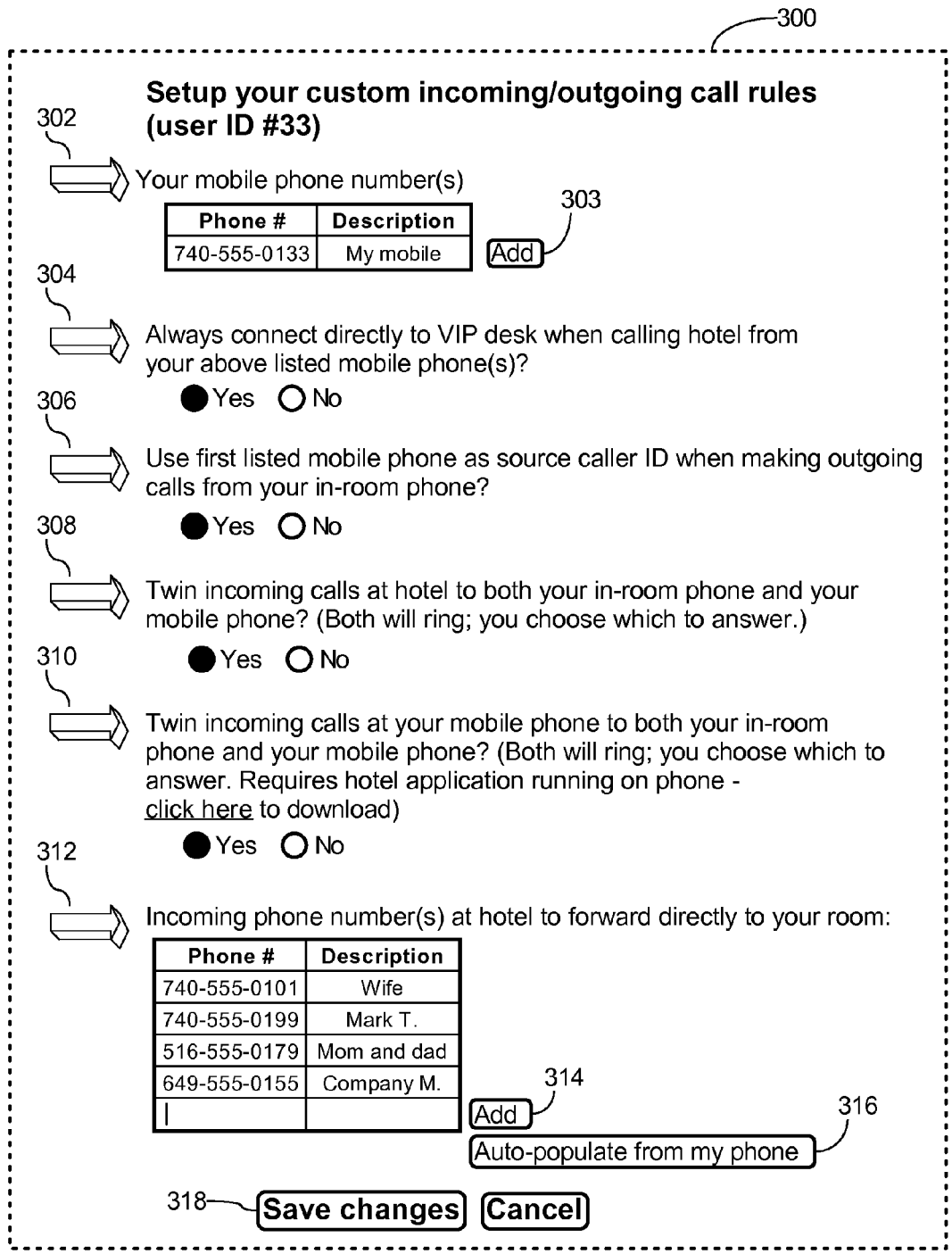
FIG. 3 shows an example user interface (UI) screen that allows a user to create various custom call rules for activation when the user checks in to a hotel participating in the system of FIG. 1.

The custom incoming call rules may be created by a user while making a reservation at the hotel 102a via the hotel chain reservation system 107. FIG. 3, described in more detail later, shows an example UI screen 300 that allows a user to create various custom call rules. Alternatively, a web based interface may be offered to a user from the cloud PBX server 120. In both examples, the newly created custom rules are then stored in the user custom call rules 148 in storage media 146 at the cloud PBX server 120.

At step 204, the user is enabled to setup voice mail that will be used while the guest is staying at one of the hotels 102. Voice mail settings that may be configured at this step include the outgoing greeting, the number of rings before answer, whether to forward to voice mail utilizing the cloud or onsite PBX servers 120, 104 or to disable voice mail on those servers and instead allow the user's mobile phone 124 to perform voice mail functions for incoming calls. The outgoing greeting may be automatically retrieved, download, or recorded by the cloud PBX server 120 from the voice mail on the user's existing voice mail account at the telecom provider 118. Alternatively, the outgoing greeting can be automatically set up in this manner by the onsite PBX server 104 at the time of the guest's check-in to the hotel 102a.

At step 206, the system 100 stores one or more custom outgoing call rule(s). In this embodiment, custom outgoing call rules refer to rules that will change the source caller ID phone number on outgoing calls made from an in-room guest phone 108 to something other than the phone number of the hotel 102a or the phone number of the guest room 112. For example, the user may setup a custom rule so that when making an outgoing call from the in-room phone 108 in the guest's assigned hotel room 112, the caller ID on the call will show up as if the guest had made the call from his or her personal mobile phone.

At step 208, the onsite PBX server 104 detects whether the user has checked in to the hotel. In this embodiment, guest check-ins are managed by the PMS 114 and therefore the onsite PBX server 104 will check the status of the user's check-in by querying the PMS 114. In another example, the PMS may automatically send check-in messages to the onsite PBX server 104 to announce the check-in of each user. Different users may be distinguished from one another according to assigned user identifiers, which may be assigned loyalty program member identifier. For example, a particular user may join the loyalty program and be assigned a user identifier of No. 33, for example. When this user makes a reservation at the hotel chain reservation system 107 they will include their loyalty program member number in order to obtain membership benefits such as points or free upgrades etc. Likewise, a user who simply arrives at a hotel without a reservation will present their loyalty program member identifier upon check-in. When determining that a particular user identifier has now checked-in, the onsite PBX server 104 will proceed to step 212 to activate any custom call rule(s) for that user. Likewise, when determining that a particular user identifier has now checked-out, the onsite PBX server 104 proceeds to step 210 to de-active any custom call rule(s) for that now checked-out user.

At step 210, the onsite PBX server 104 deletes from the active user custom call rules 138 any custom call rules for the now checked-out user. For example, in response to receiving from the PMS 114 a notification message the guest having user identifier No. 33 has now checked out of hotel 102a, the onsite PBX server 104 will delete the rules associated with user identifier No. 33 in the active user custom call rules 138. FIGS. 4 and 5, described in more detail later, provide examples of active incoming and outgoing call rules.

At step 212, the hotel will use the default incoming and outgoing call rules for any users that do not have specific rules in the active user custom call rules 138. For example, after the guest having user identifier No. 33 checks out of the hotel 102a, any incoming calls from the guest's mobile phone 124 will ring to the hotel front desk according to the default rule, any incoming calls from the guest's friends and family will ring to the front desk, and any outgoing calls made from the guest room 112a previously assigned to the guest (and now vacant or occupied by another guest lacking custom outgoing call rules) will have a source caller ID of the hotel's main phone number.

At step 214, the onsite PBX server 104 adds to the active user custom call rules 138 all of the custom call rules for the newly checked-in user. For example, in response to receiving from the PMS 114 a notification message that the guest having user identifier No. 33 has now checked in to the first guest room 108a at the hotel, the onsite PBX server 104 will retrieve the user's custom call rules from the cloud PBX server 120 and then store them as active rules in the active user custom call rules 138 on the onsite PBX server 104.

At step 216, the onsite PBX server 104 detects whether an outgoing call is made from the user's assigned guest room, i.e., in this example, the first guest room 112a. When yes, control proceeds to step 218 to change the caller ID on the call according to the user's custom outgoing call rule; alternatively, when no, control proceeds to step 220.

At step 218, the onsite PBX server 104 directs the call to the telecom phone network 118 via the cloud PBX server 120 and transmits as the source caller ID the phone number as specified in the user's custom outgoing call rule. In one beneficial usage, the user will have previously entered their own mobile phone's phone number during step 206, thus, the outgoing call made from the in-room phone 108 in the user's assigned guest room 112a will appear from its source caller ID to have been made from the user's mobile phone 124. Making the outgoing call have the caller ID of the user's own mobile phone 124 is advantageous so that the recipient of the call, for example, one of the external phones 116 shown in FIG. 1, will recognize the caller ID of the guest when receiving the call. Additionally, in many cases, the recipient of the call (e.g., external phone 116a) may have already programmed in an address book the guest's mobile phone number and will therefore display all the programmed details of the guest just as if they had have used their own mobile device 124 to make the call. In the event that the person at the external phone 116 needs to call the guest back, they can simply call use their phone's call-back functionality to dial the same number that called them, i.e., the phone number of the guest's mobile phone 124. Further, if they send back a text message instead of calling, the text message will safely arrive at the guest's mobile phone 124. Additionally, because the number reported as the caller ID is the phone number of the guest's own personal mobile phone 124, there is no concern that by the time they call back the guest will already have checked out the hotel 102a.

At step 220, the cloud PBX server 120 checks whether the hotel is receiving an incoming call. In this configuration, the hotel is pre-assigned a main telephone number in the local area where it resides and or a toll free number such as a 1-800 number. The telecom phone network is configured such that when a call is placed to the hotel's main number, the call is actually placed to the cloud PBX server 120. The cloud PBX server 120 will then notify the onsite PBX server 104 of the incoming call and will pass the call to the onsite PBX server 104. Session initiated protocol (SIP) may be used for passing the incoming call from the cloud PBX server 120 to the onsite PBX server 104. When there is an incoming call at the onsite PBX server 104, control proceeds from step 220 to FIG. 222; alternatively, when no incoming call is received at the onsite PBX server 104 from the cloud PBX server 120, control returns to step 208 to detect whether the guest is still checked in or whether the guest has now checked out.

At step 222, the onsite PBX server 104 checks the caller ID of the incoming call to determine whether it matches one of the currently checked in users' mobile phone number. As mentioned above for step 202, a user may setup a custom rule specifying that all calls originating from the user's mobile device's phone number should be directed to the hotel VIP desk. When this user is checked in to the hotel, this custom rule will be activated (at step 214). Thus, at step 222, the caller ID of the incoming call is compared with the phone numbers stored for the mobile phones of all the currently checked in guests. If there is a match for a particular user, control proceeds to step 222; alternatively, if no match is found, control proceeds to step 228.

At step 224, the onsite PBX server 104 queries the hotel PMS 114 to find the particular user's room. The user's unique identifier can be utilized to correlate the custom rule with the matching mobile phone number to that user's assigned room in the PMS 114. For example, if the incoming call's caller ID matches the mobile phone number of user identifier #33, then the onsite PBX server 104 queries the hotel PMS 114 to lookup the guest room 112 that is assigned to the guest having user identifier #33. Once found, the caller ID information on the incoming call is changed at this step to indicate the guest room. The reason this step is performed is so that the VIP desk will immediately see the guest room and all the pertinent details associated with the incoming call and will not need to waste time asking the caller for this information.

At step 226, the onsite PBX server 104 forwards the incoming call to the custom destination (i.e., the VIP desk in this example) according to the matching custom rule. In this way, the user may at any time call the hotel's main telephone number using the user's mobile phone and the user will be directly connected with the VIP desk, who will also already know the user's assigned room number and other pertinent information.

At step 228, the onsite PBX server 104 checks whether the caller ID of the incoming call matches any of the other active custom rules with specified source phone numbers. As mentioned above, users may specify the certain phone numbers for direct connection to the user's assigned guest room. If the onsite PBX server finds one of these rules matches for a particular user (e.g., user identifier #33), control proceeds to step 230; otherwise, control proceeds to step 238.

At step 230, the onsite PBX server 104 queries the hotel PMS 114 to find the particular user's room. Similar to step 224, if the incoming call's caller ID matches a custom rule for user identifier #33, then the onsite PBX server 104 queries the hotel PMS 114 to lookup the guest room 112 that is assigned to the guest having that user identifier (#33).

At step 232, the onsite PBX checks the user's custom call rules to determine if call twining is enabled. Call twinning involves giving the user an opportunity to answer the incoming call on either of their in-room phone or their personal mobile phone. When call twinning is enabled, control proceeds to step 236; otherwise, if call twinning is not required, control proceeds to step 234.

At step 234, the onsite PBX server 104 forwards the incoming call to the user's assigned in-room phone 108. The user can thereby answer the call on the in-room phone 108. In another example, the user may store a custom incoming call rule to answer all incoming calls on their mobile phone 124 and never on the in-room phone 108. To accommodate this rule, the call would be forwarded at step 234 to the user's mobile phone 124.

At step 236, the onsite PBX server 104 forwards the incoming call to a ring group consisting of both the user's mobile phone 124 and the in-room phone 108 in the user's assigned guest room 112. The user may therefore answer the call on either of the two devices 124, 108. Part of this step may involve the onsite PBX server 104 or the cloud PBX server 120 sending a notification that the incoming call to the user's mobile phone is a twinned call being sent from the hotel's PBX 104. (See step "From hotel PBX?" of FIG. 7) In this way, the hotel application 610 (see FIG. 6) running on the user's mobile phone knows to avoid re-forwarding the incoming call back to the hotel's main number.

At step 238, the onsite PBX server 104 determines whether the incoming call is a being forwarded to the hotel's main number by the mobile phone 124 of a currently checked in guest. If configured to do so by the user, the hotel application 610 running on the user's mobile phone 124 will automatically activate a call twinning feature when it detects that the user has checked in to the hotel (for example, by receiving a message from the onsite PBX server 104 as a result of the PMS 114 notifying of user check-in). In this configuration, the mobile phone 124 will forward all incoming calls received at the mobile phone 124 to the hotel's main phone number as long as the incoming call is not a call that is being forwarded to the mobile phone 124 from the hotel's onsite or cloud PBX servers 104,120. At step 238, if the incoming call is a call that is being forwarded to the hotel's main number by the user's mobile phone 124, control proceeds back to step 230. The onsite PBX server 104 can determine that the incoming call is being forwarded to the hotel's main number by receiving a notification of this fact from the user's mobile phone 124 along with details of the incoming call such as caller ID and destination mobile phone number. As explained above, from step 230 the user's room is determined and then the call is forwarded either 1) to only the user's in-room phone 108 (or only the user's mobile phone 124) if call twinning is not desired, or to both the user's in-room phone 108 and the user's mobile phone 124 if call twinning is desired by the user.

Usually it will be the case that the user desires the call twinning feature to be activated on both the user's mobile phone 124 and at the onsite PBX server 124. In this mode, when one of the user's friends or other predetermined number calls the hotel during the time that the user is checked in the hotel 102, the caller ID will be recognized at step 228 and both the user's in-room phone 108 and the user' mobile phone 124 will ring at step 236. Also in this mode, when any call from an external telephone number 116 is received at the user's mobile phone 124 during the time that the user is checked in to the hotel 102, the user's mobile phone 124 will forward the call to the hotel's main phone number, the onsite PBX server 104 will recognize the incoming call as being forwarded from the user's mobile device 124 at step 238, and both the user's in-room phone 108 and the user's mobile phone 124 will ring at step 236. If the user is in their guest room 112 at the time of the call they may prefer to take the call on the in-room phone 108 due to better voice quality or lack of cell phone coverage in their room. Alternatively, if the user is outside of their room at the time of the call, their mobile phone 124 will still ring and they can answer it just like they could a normal call.

At step 240, because none of the custom incoming or outgoing call rules of the currently checked in guests at the hotel (i.e., none of the active custom call rules) match the characteristics of the incoming or outgoing call, the default rules set up by the hotel administrators at step 200 are used. For example, an outgoing call will have the hotel's main phone number as its caller ID value and an incoming call will be forwarded to the hotel's automated attendant, front desk, or other default destination.

FIG. 3 shows an example user interface (UI) screen 300 that allows a user to create various custom call rules for activation when they are checked into a hotel 102 participating in the system 100 of FIG. 1. In this embodiment, the UI screen 300 is a web page form that can be filled out by the user either on their mobile phone 124 or another computer with a web browser (not shown) before or after the user's arrival at the hotel. In some configurations, the hotel chain may allow users to set up custom call rules as a feature of their loyalty programs when making a reservation at hotel chain reservation system 107. In another configuration, the loyalty program may be administrated by a vendor of the PBX system 100 and may work across different hotels 102 belong to multiple chains. In such a case, users may fill out UI screen 300 at another web server (not shown) coupled to the Internet 106.

In FIG. 3, the user is assumed to have user identifier #33. When the user checks in to a hotel 102, they also provide this user identifier to the hotel for storage along with the user's details in the PMS 114. This process may be automated by the user identifier being sent to the hotel 102 along with the reservation details from the reservation system 107.

The user interface screen 300 includes a first setting 302 allowing the user to enter the phone number of their mobile phone 124. Usually a user will only have a single mobile phone number but an add button 303 is provided to allow the user to enter multiple phone numbers in the event they carry multiple cell phones.

A second setting 304 allows the user to configure a custom incoming call rule so that when the user calls the hotel's main phone number using their mobile phone 124 (i.e., the listed phone number from setting 302), the call will be directly connected to the VIP desk. This setting 304 corresponds to steps 222, 224, and 226 in FIG. 2.

A third setting 306 allows the user to configure a custom outgoing call rule so that when the user makes an outgoing call from the in-room phone 108 of their assigned guest room 112, the call will have a caller ID of the user's mobile phone 124 (i.e., the first listed phone number from setting 302). This setting 306 corresponds to steps 216 and 218 of FIG. 2.

A fourth setting 308 allows the user to configure a custom incoming call of whether to twin calls at the hotel. When enabled, incoming calls received from external phones 116 at the hotel's main number that are forwarded to the user's assigned room 112 will be twinned so that they can be answered at both the user's mobile phone 124 and the in-room phone 108 in the user's assigned room 112. Calls received from external phones 116 at the hotel's main number refers to calls that directly dial the hotel's main number, incoming calls that are forwarded to the hotel's main number by the user's mobile phone (e.g., step 238 "yes branch"), and incoming calls that are forwarded to the user's room 112 either due to matching the user's list of predetermined phone number (see below explanation of setting 312) or because the auto-attendant or the hotel front desk has forwarded the call to the user's room 112. This setting 308 corresponds to steps 232, 234, and 236 of FIG. 2.

A fifth setting 310 allows the user to configure a custom incoming call of whether to twin calls at the user's mobile phone. When enabled, incoming calls received at the user's mobile phone 124 will be forwarded to the hotel's main phone number as long as the call is not being forwarded to the user's mobile phone 124 from the onsite and/or cloud PBX server 104, 120. This setting 310 corresponds to step to step 238 of FIG. 2 and involves the hotel application 610 running on the mobile device 124.

A sixth setting 312 allows the user to configure a number of custom incoming call rules to forward various telephone numbers specified by the user directly to the user's assigned room 108. An add button 314 is provided to allow the user to add additional numbers to the table and the table may also be auto-populated 316. Auto-population 316 may involve presenting a pop-up message to the user with a phone number to send an SMS message with the phone/name list to the cloud PBX server 120, which then displays the list under setting 312. An email address may also be presented to the user to allow them to email the list to for auto-populating setting 312. This setting 312 may be utilized by a guest who wants calls to ring directly to their in-room phone 108a. If the specified number recognized via automatic number identification (ANI) comes into the hotel, then it bypasses the automatic attendant (or other default destination) and rings direct to the in-room phone 108a of the guest (i.e., guest have user ID #33). As soon as the guest checks out, these incoming calls will be directed to the attendant.

Once the user has configured their custom call settings, the user can press the save button 318 and the changes will be saved in the storage media 146 as part of the user custom call rules 148. Thereafter, as the user checks in to the various hotels 102 participating in system 100, the users custom rules will be sent from the cloud PBX server 120 to the onsite PBX server 104 for activation as active custom call rules 138. Likewise, when the user checks out of the hotel 102, the user's custom rules are deleted from the activate custom call rules 138 at that hotel but remain in the cloud-stored user custom call rules 148 so that they can be activated when the user checks into a next hotel 102.

FIG. 4 shows example active incoming call rules 138a stored at the onsite PBX server 104 at the hotel 102a while the example guest having user identifier #33 is checked in to the hotel 102a. As illustrated, the active incoming call rules 138a are organized in a database table where each row has a user ID column 400. Rows 420, 422, and 424 with the user ID column 400 set equal to "33" are custom rules for the guest having user ID #33. These rows correspond to the various settings 302, 304, 308, 310, and 312 configured by the user via the UI screen 300 shown in FIG. 3. Other users who are also currently checked in to the hotel 102a may have their own custom incoming call rules (not shown) stored in the database table. Additionally, a default rule at row 426 has "*" as the user ID and is therefore applicable to all users; row 426 is the default incoming call rule that applies when none of the above row user-specific rows applies. The default incoming call rule at row 426 corresponds to the hotel administrator's default settings configured at step 200 of FIG. 2.

FIG. 5 shows example active outgoing call rules 138b stored at the onsite PBX server 104 at the hotel 102a while the guest having user identifier #33 is checked in to the hotel 102a. These rules are also stored in a database table; where row 500 corresponds to setting 306 regarding the caller ID on outgoing calls as configured by the user on UI screen 300. Row 500 is the custom outgoing call rule for the current guest of the having user ID #33 while row 502 is a default outgoing call rule as setup by the administrator at step 200 of FIG. 2. Further, other users who are also currently checked in to the hotel 102a may have their own custom outgoing call rules (not shown) stored in the database table.

Figure 6:
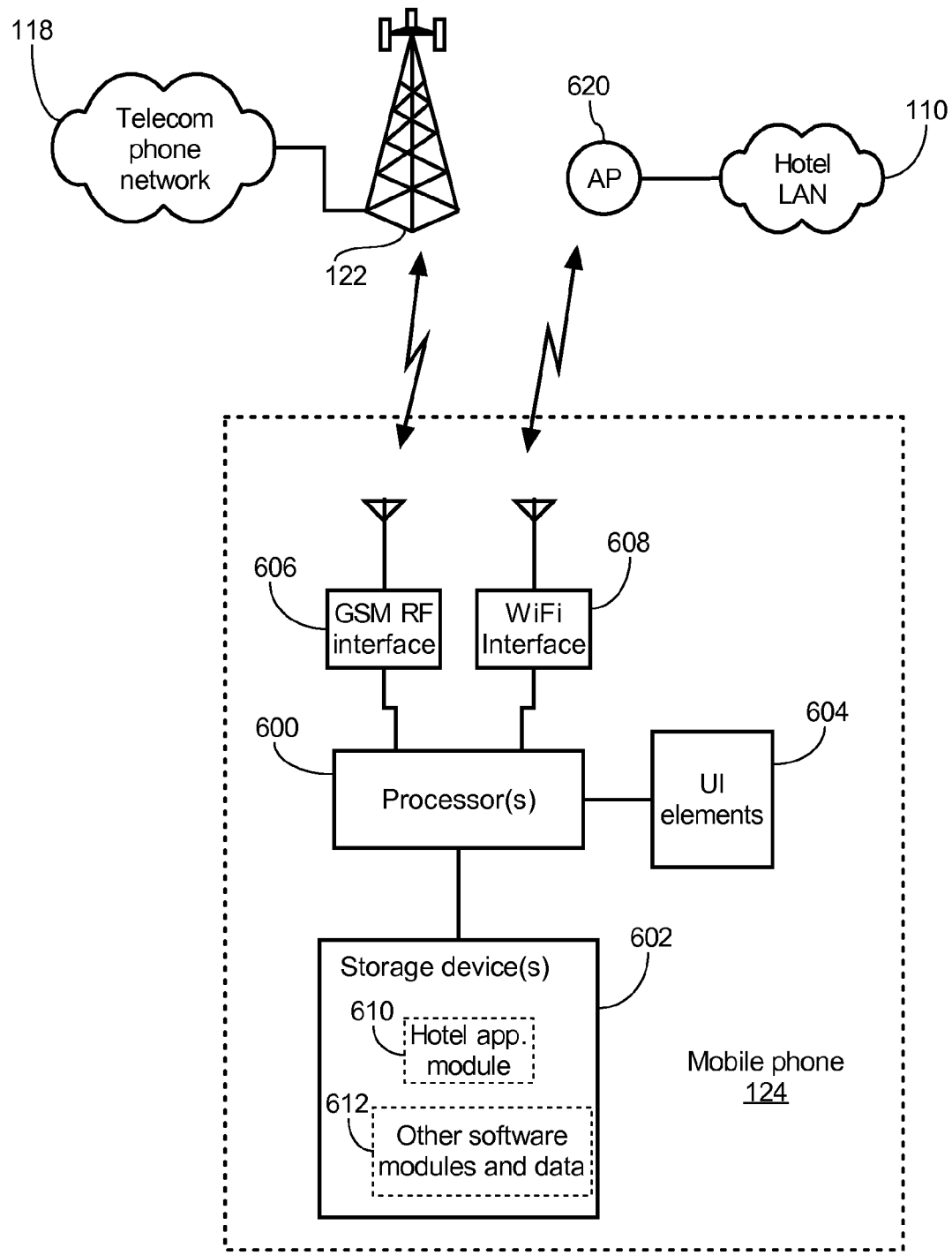
FIG. 6 is a block diagram of a mobile phone for running a predetermined hotel application installed thereon.

FIG. 6 is a block diagram of the user's mobile phone 124; as shown, the mobile phone includes one or more processors 600 coupled to one or more storage devices 602, user interface UI elements 604, a global system for mobile communications (GSM) radio frequency (RF) interface 606, and a WiFi (IEEE 802.11) interface 608 for communicating wirelessly with one more access points 620 forming a part of the hotel LAN 110 at the hotel 102a. Other types of communications interfaces may also be included in other configurations such as Bluetooth and/or other types of wireless local area network (WLAN), for example. In this configuration, the one or more processor(s) 600 load and execute a hotel application module 610 stored on the storage device 602 in order to provide functions of the hotel predetermined application as described below. The application 610 may be installed by the user of the mobile device 124 purchasing or freely installing the application from an application store or other software repository available on the Internet (e.g., by the user clicking the download link provided on the UI screen 300 under setting 310).

Figure 7:
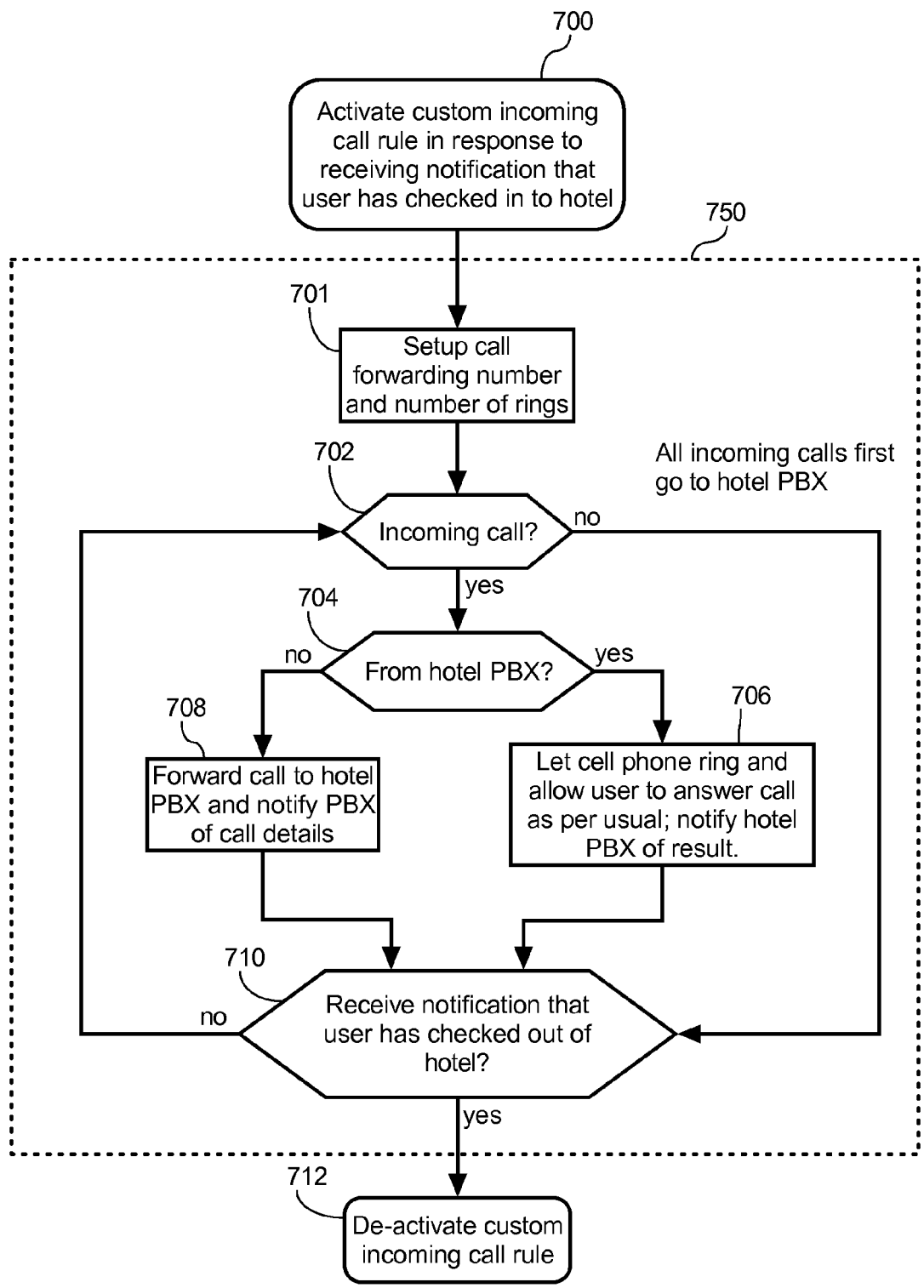
FIG. 7 shows a method of processing telephone calls by the hotel application running on the mobile device of FIG. 6 according to an exemplary embodiment of the invention where all incoming calls are first forwarded to the hotel by the user's mobile phone.

FIG. 7 shows a method of processing telephone calls by the hotel application 610 running on the mobile device 124 according to an exemplary embodiment of the invention. In this embodiment, all incoming calls at the mobile phone are automatically redirected by the mobile phone 124 to the hotel's main phone number via cloud/onsite PBX servers 120, 104 before possibly being twinned back to the mobile phone 124 and actually causing the mobile phone 124 to ring. Whether or not the incoming call is forwarded back to the user's mobile device is dependent upon the user's custom incoming call rules as configured in setting 310 of FIG. 3. The collection of steps 750 of FIG. 7 work in tandem with the steps 250 shown in FIG. 2 and in this mode as labeled in the Figures "all incoming calls first go to hotel PBX."

The steps of FIG. 7 are generally performed by the one or more processors 700 of the mobile phone 124 pursuant to the software of the hotel application module 610 working in conjunction with other software modules and data 712 providing pre-existing functionality on the mobile phone such as the ability to receiving incoming calls, perform call forwarding, sound the phone's ringing mechanism etc. The steps of the flowchart are not restricted to the exact order shown, and, in other configurations, shown steps may be omitted or other intermediate steps added. In this embodiment, the mobile phone 124 operates as follows:

The process starts at step 700 with the activation of the custom incoming call rules by the hotel application 610 in response to the hotel application 610 receiving a notification that the user of the mobile phone 124 has checked in to the hotel 102a. The notification may be received from the onsite PBX server 104 at step 214 of FIG. 2 activating the user's custom call rules when the user checks in to the hotel 102. In an example, when the user arrives in the vicinity of the hotel, the hotel application 610 detects the hotel LAN 110 via access point 620 and associates itself. The app. 610 may then query a known address of the onsite PBX server (e.g., configured as the default gateway on hotel LAN or another known address, either internet protocol (IP) address or universal resource locator (URL), in order to notify the onsite PBX server 104 of the user identifier (e.g., ID #33) of the phone's 124 user. Thereafter, when the onsite PBX server 104 receives a notification from the hotel's PMS 114 that a guest having user identifier #33 has checked in to the hotel, the onsite PBX server 104 will notify the hotel app. 610 on the guest's phone 124 and the process will begin at step 700 in order to activate call forwarding from the mobile phone 124 to the hotel 102a. The actions of the mobile phone 124 while this feature is activated are shown in FIG. 7 as the collection of steps 750, each described below.

At step 702, the hotel application 610 reconfigures the mobile phone 124 and/or the telecom network 118 to configure a default call forwarding as the hotel's main phone number and a number of rings sufficient for the user to answer an incoming call. Mobile phones 124 typically have the capability to forward incoming calls to a configurable voice mail phone number after a predetermined number of rings. At step 701 the hotel application may store a record of the phone's current settings and then change the voice mail phone number setting so that rather than forwarding an unanswered call to the user's telecom based voice mail phone number, the unanswered call will be forwarded to the hotel's main phone number.

The hotel application also makes sure that the number of rings is sufficient to give the user around ten to twenty seconds to answer an incoming call before the phone will automatically forward the call to the hotel's phone number. Typically, the phone 124 will preset to provide a number of rings such as five rings before automatically forwarding to voice mail so the ring settings in the phone 124 may already be okay; however, if the phone 124 was previously set to immediately forward to the configured voicemail number, the hotel application would change to a higher number of rings such as five to ten. The reason is the hotel application 610 will trigger the forwarding immediately only for some incoming calls rather than the phone immediately performing forwarding for all incoming calls.

At step 702, the hotel application 610 determines whether there is an incoming call at the mobile device 124. The hotel application may access one or more application programming interfaces (API) provided by the other software modules 612 on the phone 124 to set up an interrupt to occur when an incoming call is received. When an incoming call is received, control proceeds to step 704; otherwise, the hotel application proceeds to step 710 to check whether the phone's user is still checked in to the hotel 102a.

At step 704, the hotel application 610 determines whether the incoming call is being forwarded to the mobile phone 124 by the onsite and/or cloud PBX server(s) 104, 120. The hotel application 610 does this by communicating with onsite PBX server 104 via the WiFi interface 608 and the hotel LAN 110 to check whether the onsite PBX server 104 is currently forwarding a call to the mobile phone (e.g., to check whether the onsite PBX server 104 has just performed either of steps 234 and/or 236 in FIG. 2). Alternatively, the onsite PBX server 104 may send a notification message to the phone 124 via hotel LAN 110 or the Telecom network 118 when forwarding a call to the phone 124. In this configuration, a secondary channel via the hotel LAN 110 or the Telecom network 118 is utilized to indicate whether the incoming call is being forwarded from the hotel 102a because the caller ID information on the incoming call is preserved so that the user's phone will continue to display the proper information of the caller, e.g., the phone number and name of one of the external phones 116 in FIG. 1. When the incoming call is being forwarded from the onsite or cloud PBX server 104, 120, control proceeds to step 706 to allow the user to answer the call; alternatively control proceeds to step 708 to trigger the phone to forward the call to the onsite PBX server 120 (i.e., the handler of the hotel's main phone number).

At step 706, the hotel application 610 allows the user's mobile phone 124 to ring and gives the user an opportunity to answer the incoming call. When the call is answered by the user, the hotel application 610 sends a notification to the onsite PBX server 104 that the call is answered. The onsite PBX server 104 will, in response, stop ringing the in-room phone in the user's assigned guest room 112. The call is now connected to the mobile device 124 and the user may hold the conversation utilizing the mobile phone 124. Alternatively, when the incoming call is not answered by the user, the hotel application 610 sends a notification to the onsite PBX server 104 that call went unanswered. In this manner, when the call is re-forwarded back to the hotel's main phone number, the cloud PBX server 120 can send it directly to voice mail (either at the cloud PBX server or the user's originally configured telecom voice mail number stored at step 701).

At step 708, the hotel application 610 forwards the call to the hotel's main phone number, and the call is thereafter passed from the cloud PBX server 120 to the onsite PBX server 104. The hotel application 610 is also in communication with the onsite PBX server 104 via the hotel LAN 110 and the hotel application 610 utilizes this communication channel in order to notify the onsite PBX server 104 that the call is being forwarded from the user's mobile phone. In this way, at step 238 of FIG. 2, the onsite PBX server 104 is able to determine that the incoming call is being forwarded and therefore proceeds via the "Yes" step to step 230. In order to actually forward the call, the hotel application 610 may simulate the user pressing the "End Call" button. On a typical phone this will cause the incoming call to be immediately forwarded to the preconfigured voice mail number (i.e., the main phone line of the hotel as a result of step 701 in FIG. 7). Alternatively, the other software modules 612 running on the phone may support an API command to directly forward an incoming call to the preconfigured voice mail number or a specified number sent in a parameter via the API.

At step 710, the hotel application 610 determines whether the user of the mobile phone 124 is still checked in to the hotel 102a. This may be done by polling the onsite PBX server 104 via the hotel LAN 110, for example. In another example, the onsite PBX server 104 may receive a notification message from onsite PBX server 104 when the user checks out of the hotel 102a. The onsite PBX server 104 is aware of the checkout at step 210 by receiving a check-out message for the user ID of each checked out guest from the PMS 114. In response to the user of the mobile phone 124 checking out of the hotel 102, the hotel application 610 proceeds to step 712 to de-activate the custom incoming call rule at the mobile phone 124. Alternatively, if the user is still checked in to the hotel 102a, control returns to step 702 to wait for another incoming call.

At step 712, the hotel application 610 deactivates call forwarding to the hotel 102a by reconfiguring the mobile phone 124 with the telecom voice mail number and number of rings as were previously programmed on the mobile phone 124 before the hotel call forwarding feature was activated. As previously described, the hotel application 610 may store the original values of these settings at step 701. Now that the user has checked out of the hotel, the phone is returned to those stored settings.

Figure 8:
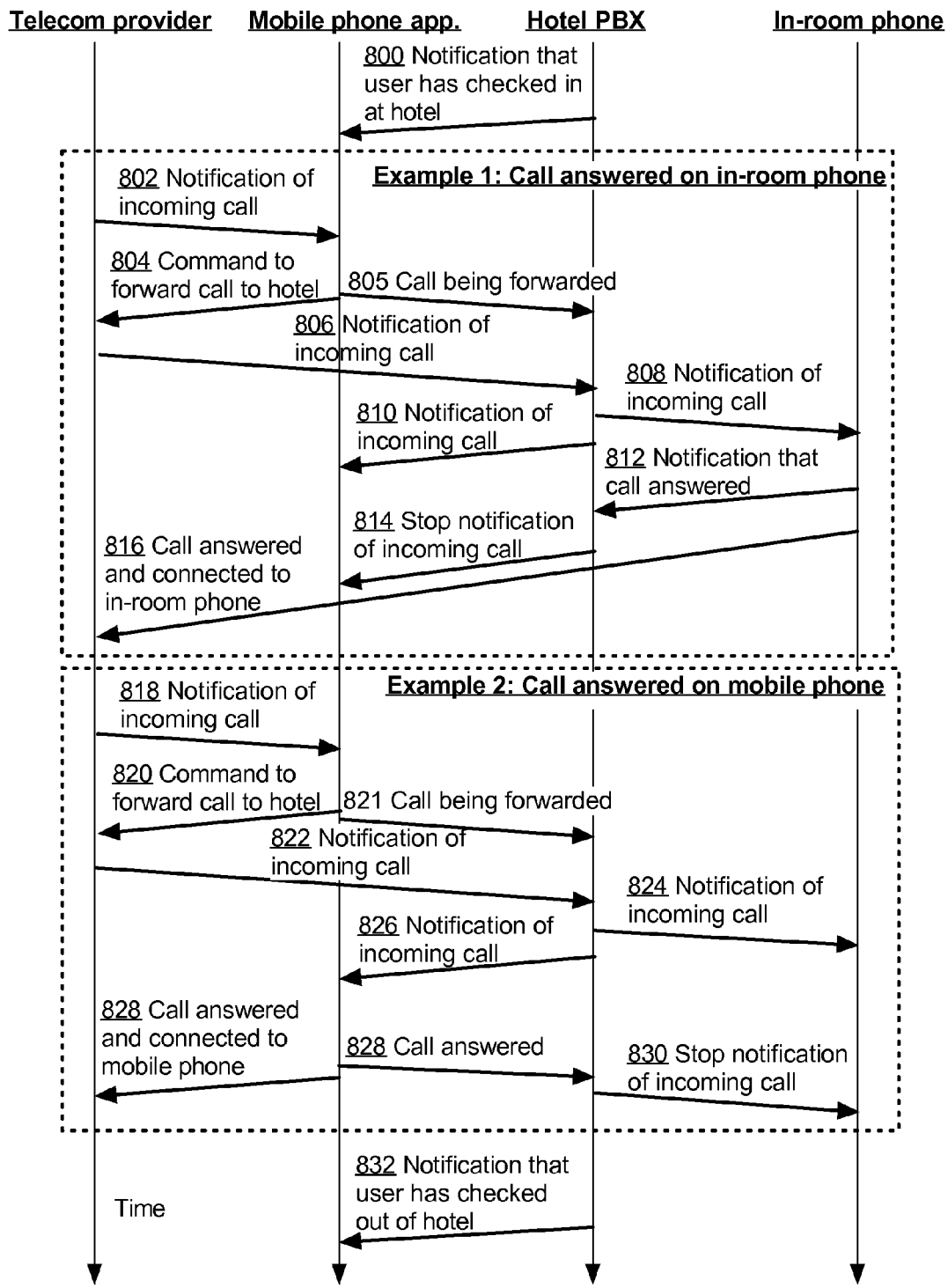
FIG. 8 shows a timeline diagram of interactions between the telecom provider network, the hotel application running on the user's mobile phone, the hotel PBX server, and the in-room phone of the user's assigned guest room when applying the methods of FIG. 2 and FIG. 7.

FIG. 8 shows a timeline diagram of call notification and transfers, and other interactions between the telecom provider network 118, the hotel application 610 running on the user's mobile phone 124, the hotel PBX (i.e., cloud and/or onsite PBX servers 120, 104), and the in-room phone 108a of the user's assigned guest room 112a. The timeline diagram of FIG. 8 corresponds to the above-described embodiment shown in FIG. 2 at steps 250 and FIG. 7 steps 750 where all incoming calls first go to the hotel PBX.

In FIG. 8 the timeline begins after the user of the mobile phone 124 has checked in to the hotel 102a. The hotel PBX (e.g., onsite PBX server 104) sends a notification 800 via hotel LAN 110 (or other communication channel) to the hotel application 610 that the user of the mobile phone 124 has now checked in to the hotel. The notification message 800 may provide the hotel app. 610 with the main phone number of the hotel 102a (i.e., a phone number assigned to the cloud PBX server 120) as the number to which future incoming calls should be forwarded (i.e., at step 708 of FIG. 7).

A notification 802 of an incoming call from telecom provider 118 is then received by the hotel app. 610 on the mobile phone 124. In this example the call is a new call from an external phone 116 that is not being forwarded to the mobile phone 124 by the hotel PBX.

A forwarding command 804 is sent from the mobile phone 124 to the telecom provider to forward the call to the hotel; in this way the hotel app. 610 automatically forwards the call to the hotel PBX. As explained in step 708 of FIG. 7, this may be done by the hotel app. 610 activating the "End Call" button as if the user had pressed this button. On a typical phone this will cause the incoming call to be immediately forwarded to the preconfigured voice mail number (i.e., the main phone line of the hotel as a result of step 701 in FIG. 7).

The hotel app. 610 also sends a call being forwarded notification 805 to the onsite PBX server 104 (e.g., via hotel LAN 110 or another communication channel) so that the onsite PBX server 104 knows the call is being forwarded and knows the details of the call such as the mobile phone number to which it was originally directed.

As a result of the forwarding command, the telecom provider 118 sends a notification 806 to the cloud PBX server 120 of the incoming call.

The cloud PBX server 120 passes the call to the onsite PBX server 104, which twins the call at step 236 to the ring group consisting of both the user's mobile phone 124 and the in-room phone 108a in the user's assigned guest room 112a. Notification message 808 is the call going to the in-room phone 108 and notification message 810 is the call also going back to the user's mobile phone 124 along with a message that it is being forwarded to the phone 124 from the hotel's PBX.

In this example, the user is assumed to be in their guest room 112a and therefore chooses to answer the call on the in-room phone 108. The in-room phone 108a therefore sends a notification 812 to the onsite PBX server 104 that the call is now answered.

Since the call is now answered on the in-room phone 108a, the onsite PBX server 104 stops 814 the incoming call notification going to the user's mobile phone 124. The incoming call is therefore answered at and connected 816 to the in-room phone 108a.

FIG. 8 also shows another example where the user chooses to answer an incoming call on the mobile phone 124. Interactions 818, 820, 821, 822, 824, and 826 all correspond directly to the above-described interactions 802, 804, 805, 806, 808, and 810, respectively. The difference starts when the user answers the call on the mobile phone 124. When this occurs, the hotel application 610 sends a notification 828 that the call is answered to the onsite PBX server 104. The onsite PBX server then stops 830 the incoming call notification going to the in-room phone 108a. The incoming call is therefore answered and connected 828 to the user's mobile phone 124.

After the user has checked out of the hotel 102a, the onsite PBX server 104 sends a notification 832 to the hotel application 610 running on the mobile phone 124 to deactivate the custom incoming call rule (performed by the hotel app. 610 at step 712 in FIG. 7).

Figure 9:
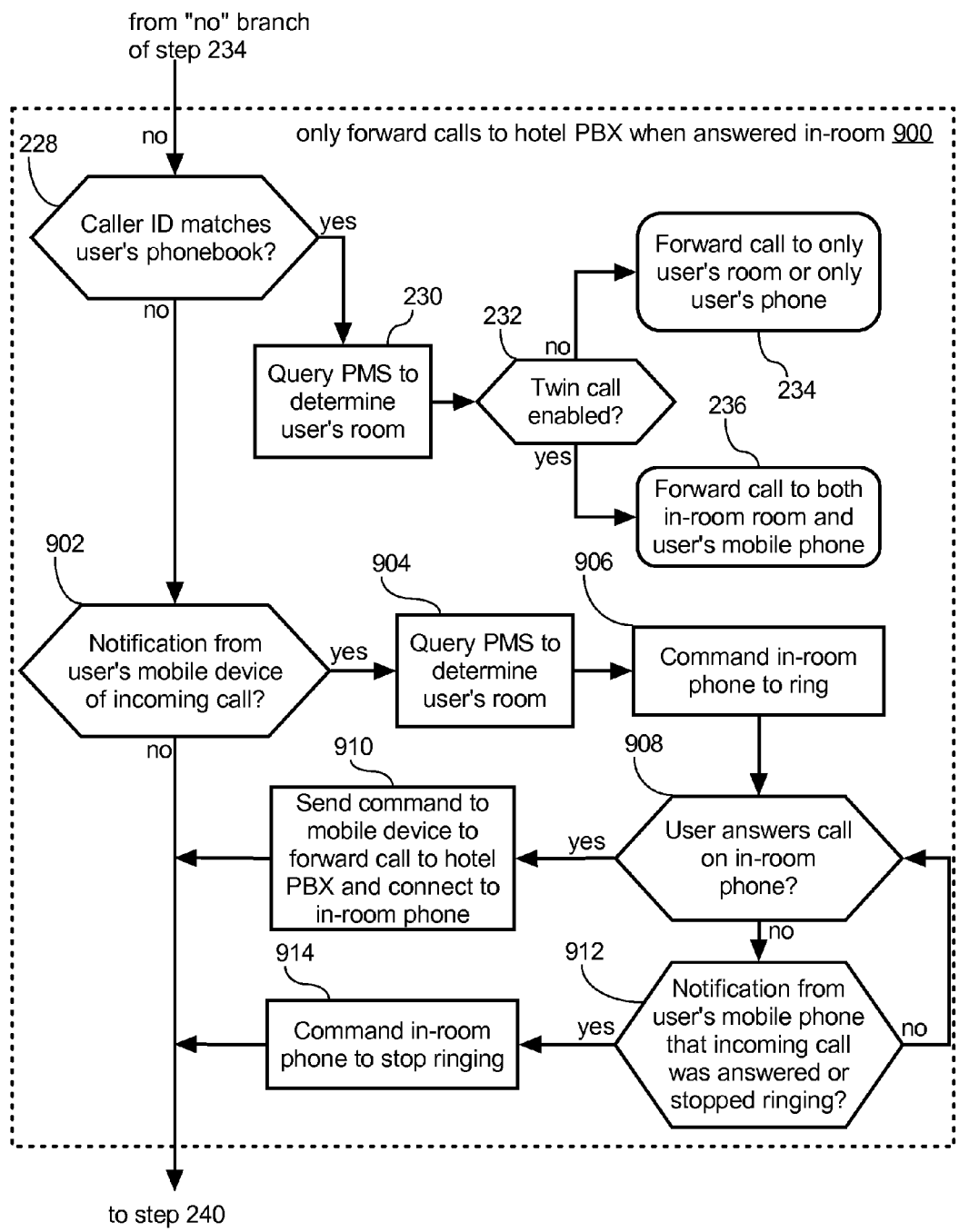
FIG. 9 illustrates a flowchart of operations performed by the onsite PBX server showing another embodiment for twinning calls from the user's mobile phone to the hotel where all only incoming calls at the mobile device that have been answered at the in-room phone are redirected to the hotel's PBX system.

FIG. 9 illustrates another embodiment for twinning calls at the mobile phone 124 to the hotel. The collection of steps 260 replace the collection of steps 250 in FIG. 2. As will be described further below, in the embodiment of FIG. 9, only incoming calls that are answered on the in-room phone 108b are actually forwarded from the mobile phone 124 to the hotel PBX 120, 104.

In FIG. 9, the initial steps 228, 230, 232, 234, 236 are similar to as previously described for FIG. 2 and a repeated description of these similarities is omitted. One difference is that when the caller ID of the incoming call does not match the user's phonebook, control proceeds from step 228 to new step 902.

At step 902, the onsite PBX server 104 checks to see whether it has received a notification of an incoming call from the hotel application 610 running on the user's mobile phone 124. The hotel application 610 may monitor incoming calls received at the user's phone while the user is checked into the hotel. When an incoming call arrives, the user's mobile phone rings as per its usual behavior; however, in the background the hotel app. 610 also notifies the onsite PBX server 104 via hotel LAN 110 of the incoming call, the user's identifier, and also forwards the caller ID information of the incoming call as well. Upon receiving such notification of an incoming call, control proceeds from step 902 to step 904; alternatively, when no incoming call is received at the mobile device 124, control proceeds to step 240 in FIG. 2.

At step 904, the onsite PBX server 104 determines the user's room according to the user identifier received at step 902. This step may involve querying the hotel PMS 114 similar to as described for step 230 earlier on.

At step 906, the onsite PBX server 104 makes a call to the in-room phone 108a of the user's assigned guest room 114 in order to cause the in-room phone 108a to ring. The caller ID information received from the user's mobile phone at step 902 is displayed on the in-room phone 108a.

At step 908, the onsite PBX server 104 checks whether the in-room phone 108a has been answered; when yes, control proceeds to step 910; otherwise, control proceeds to step 912.

At step 910, the onsite PBX server 104 sends a command via hotel LAN 110 to the mobile phone 124 instructing the hotel application 610 to forward the incoming call to the hotel's main phone number (i.e., cloud PBX server 120). When the call comes in (recognized by the caller ID information received at 902), the call is connected to the in-room phone 108a.

At step 912, the onsite PBX server 104 checks whether the notification from the user's mobile phone 124 indicates the incoming call was dropped or answered at the mobile phone 124. If yes, control proceeds to step 914 to stop the in-room phone from ringing; otherwise, control returns to step 108 to give the user more time to answer the in-room phone 108a.

At step 914, the onsite PBX server 104 cancels the notification of incoming call for the in-room phone 108a in the guest's room 112a. The phone thereby stops ringing and the user either answered the call on the mobile device directly or the call went unanswered and was sent to the user's voicemail (e.g., provided by the user's telecom provider).

Figure 10:
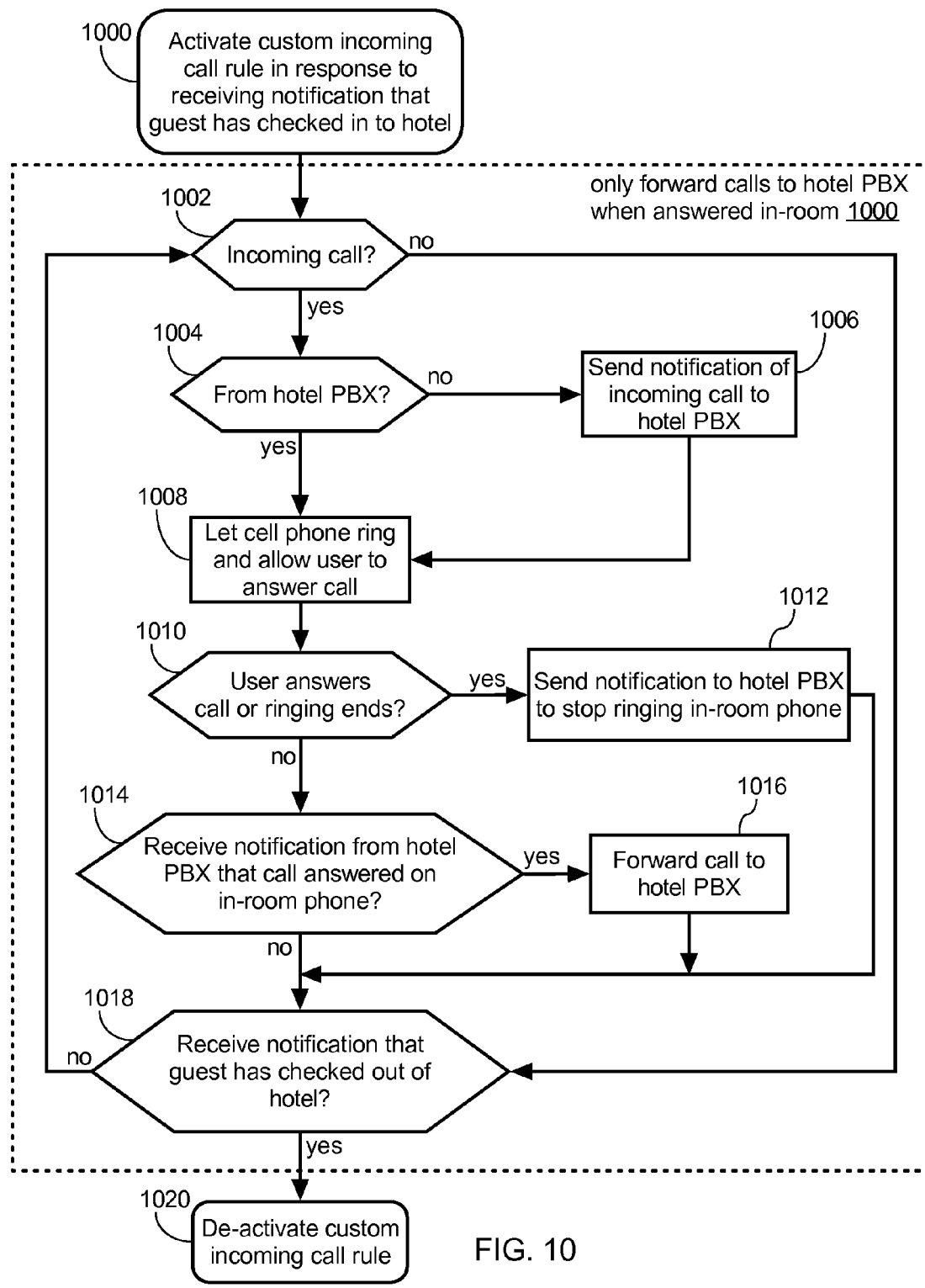
FIG. 10 shows a method of processing telephone calls by the hotel application running on the mobile device in conjunction with the method of FIG. 9.

FIG. 10 shows a method of processing telephone calls by the hotel application 610 running on the mobile device 124 according to an embodiment of the invention where only incoming calls at the mobile device that have been answered at the in-room phone 108 are redirected to the hotel's PBX system. In this embodiment, the hotel application 610 running on the user's mobile phone 124 is in communication with the onsite PBX server 104 so the PBX server 104 knows when an incoming call is received at the mobile phone 124 and the phone 124 knows when the user has picked up the in-room phone 108. Only after the user has actually picked up the in-room handset does the hotel application 610 cause the mobile phone to forward the call. Although there may be a slight delay to the guest when they pick up the in-room phone 108 before they are connected to the caller, a message may be played to the guest by the onsite PBX server 104 such as "stand by for incoming call". Furthermore, from the caller's point of view there is no appreciable delay because the call is not actually answered until after it is forwarded to the in-room phone 108. The collection of steps 1000 of FIG. 10 work in tandem with the steps 900 previously described for FIG. 9.

The steps of FIG. 10 are generally performed by the one or more processors 700 of the mobile phone 124 pursuant to the software of the hotel application module 610 working in conjunction with other software modules and data 612 providing pre-existing functionality on the mobile phone such as the ability to receiving incoming calls, perform call forwarding, sound the phone's ringing mechanism etc. The steps of the flowchart are not restricted to the exact order shown, and, in other configurations, shown steps may be omitted or other intermediate steps added. In this embodiment, the mobile phone 124 operates as follows:

Similar to FIG. 7, the process starts at step 1000 with the activation of the custom incoming call rules by the hotel application 610 in response to the hotel application 610 receiving a notification that the user of the mobile phone 124 has checked in to the hotel 102a. Similar description from step 700 is also applicable for step 1000.

At step 1002, the hotel application 610 determines whether there is an incoming call at the mobile device. This step may be performed similar to as previously described for step 702 of FIG. 7. When an incoming call is received, control proceeds to step 1004; otherwise, the hotel application proceeds to step 1020 to check whether the phone's user is still checked in to the hotel 102a.

At step 1004, the hotel application 610 determines whether the incoming call is being forwarded to the mobile phone 124 by the onsite and/or cloud PBX server(s) 104, 120. This step may be performed similar to as previously described for step 704 of FIG. 7. When the incoming call is being forwarded from the onsite or cloud PBX server 104, 120, control proceeds to step 1008; otherwise, control proceeds to step 1006.

At step 1006, the hotel application 610 sends a notification of the incoming call to the hotel PBX via hotel LAN 110. The call is not actually forwarded to the hotel at this step but instead a back channel such as a TCP connection between the hotel application 610 and the onsite PBX server 104 is utilized to pass the notification. For example, the notification is received by the onsite PBX server 104 at step 902 of FIG. 9.

At step 1008, the hotel application 610 allows the user's mobile phone 124 to ring and gives the user an opportunity to answer the incoming call.

At step 1010, the hotel application 610 determines whether the user has answered the incoming call on the mobile device 124. When yes, control proceeds to step 1012; otherwise, control proceeds to step 1014.

At step 1012, because the call was answered by the user on the mobile phone 124, the hotel application 610 sends a notification to the onsite PBX server 104 to inform the server 104 that the call has already been answered. The onsite PBX server 104 checks for this notification at step 912 of FIG. 9, and as shown in that diagram, will stop ringing the in-room phone 108a in this situation.

At step 1014, the hotel application 610 determines whether the user desires to answer the incoming call on the in-room phone 108. This is determined by receiving a notification message from the onsite PBX server 104 that the in-room phone 108 that was previously called by the onsite PBX server 104 has now been picked up (i.e., answered) by the guest. When this situation occurs, the hotel application 610 running on the mobile phone needs to forward the incoming call to the hotel's PBX system. This notification message received at the mobile phone 124 at this step 1014 was sent by the onsite PBX server 104 at step 910 of FIG. 9. When the notification that the call was answered on the in-room phone is received, control proceeds to step 1016; otherwise, control proceeds step 1018.

At step 1016, the hotel application 610 running on the mobile phone 124 forwards the incoming call to the hotel's main phone number, and the call is thereafter passed from the cloud PBX server 120 to the onsite PBX server 104 and finally to the in-room phone 108a that the user has already answered. The call is now connected to the in-room phone 108a and the user can hold the conversation via the in-room phone 108a.

At step 1018, the hotel application 610 determines whether the user of the mobile phone 124 is still checked in to the hotel 102a. This step may be performed similar to as previously described for step 710 of FIG. 7. In response to the user of the mobile phone 124 checking out of the hotel 102a, the hotel application 610 proceeds to step 1020 to de-activate the custom incoming call rule at the mobile phone 124. Alternatively, if the user is still checked in to the hotel 102a, control returns to step 1002 to wait for another incoming call.

Figure 11:
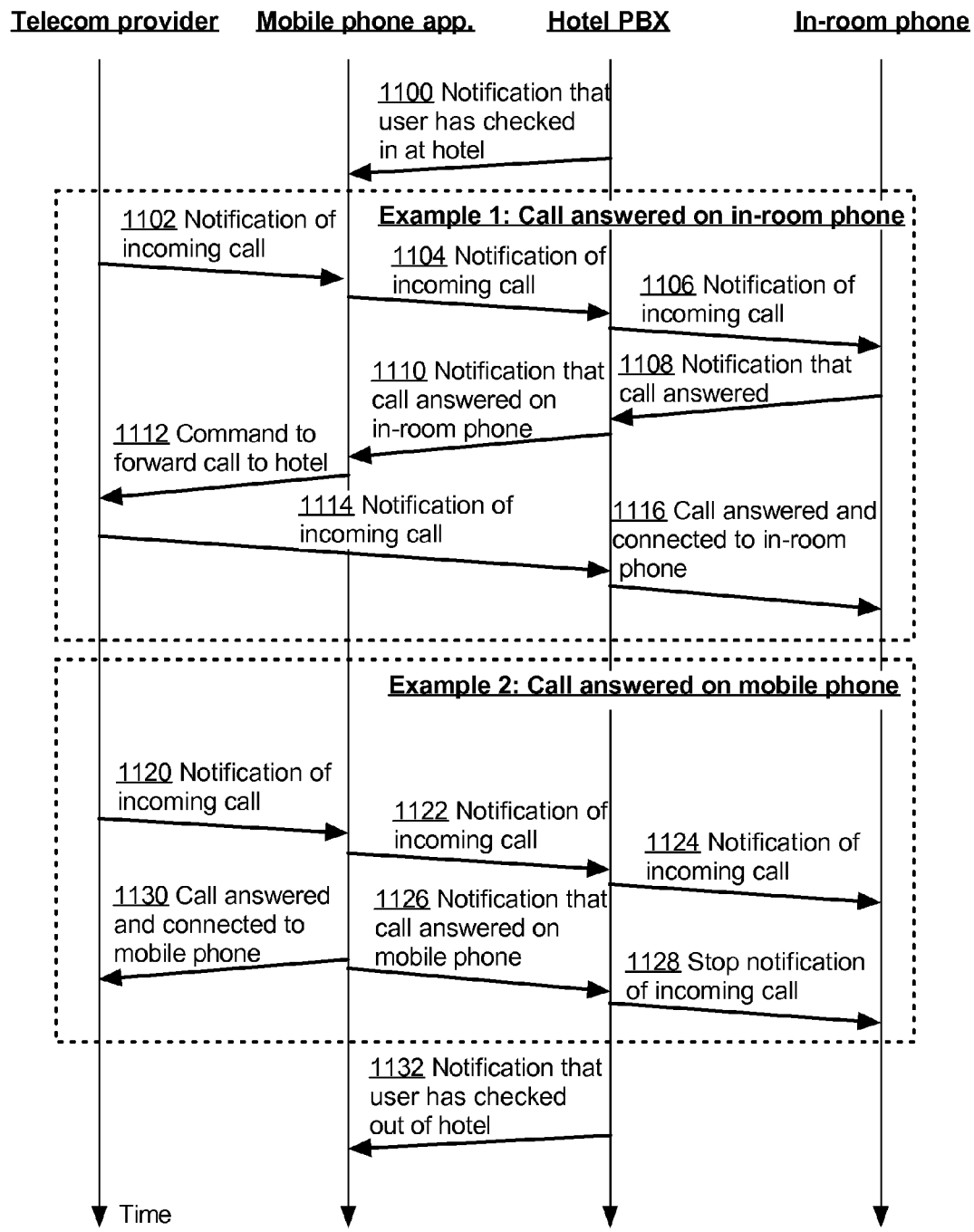
FIG. 11 shows a timeline diagram of interactions between the telecom provider network, the hotel application running on the user's mobile phone, the hotel PBX servers, and the in-room phone of the user's assigned guest room when applying the methods of FIG. 9 and FIG. 10.

FIG. 11 shows a timeline diagram of call notification and transfers, and other interactions between the telecom provider network 118, the hotel application 610 running on the user's mobile phone 124, the hotel PBX (i.e., cloud and/or onsite PBX servers 120, 104), and the in-room phone 108a of the user's assigned guest room 112a. The timeline diagram of FIG. 11 corresponds to the above-described embodiment shown in FIG. 9 at steps 900 and FIG. 10 steps 100 where only incoming calls that are answered on the in-room phone 108 are forwarded to the hotel PBX.

In FIG. 11 the timeline begins after the user of the mobile phone 124 has checked in to the hotel 102a. The hotel PBX (e.g., onsite PBX server 104) sends a notification 1100 via hotel LAN 110 (or other communication channel) to the hotel application 610 that the user of the mobile phone 124 has now checked in to the hotel. The notification message 1100 may provide the hotel app. 610 with the main phone number of the hotel 102a (i.e., a phone number assigned to the cloud PBX server 120) as the number to which future incoming calls that are answered on in-room phone 108a should be forwarded (i.e., at step 1016 of FIG. 11).

A notification 1102 of an incoming call from telecom provider 118 is then received by the hotel app. 610 on the mobile phone 124. In this example the call is a new call from an external phone 116 that is not being forwarded to the mobile phone 124 by the hotel PBX.

Next, a notification 1104 of the incoming call is sent from by the hotel application 610 to the onsite PBX server 104. Notification 1104 corresponds to step 1006 of FIG. 10.

In response to notification 1104, the onsite PBX server 104 sends a notification 1106 of incoming call to the in-room phone 108*a* of the user's registered guest room 112*a*. The notification 1106 to the in-room phone 108*a* is the result of the onsite PBX server 104 performing steps 902, 904, and 906 in FIG. 9.

In this example, the user decides to answer the incoming call at the in-room phone 108 rather than on the mobile device 124 (both are ringing at this point). After picking up the in-room phone 108*a*, a notification 1108 of the called being answered is sent from the in-room phone 108*a* to the onsite PBX server 104. This notification is received by the onsite PBX server 104 at step 908 of FIG. 9.

The onsite PBX server 104 then sends a notification 1110 that the call was answered on in-room phone 108*a* to the hotel application 610 running on the mobile phone 124. This notification 1110 corresponds to step 912 in FIG. 9.

Next, the hotel application 610 sends a command 1112 to the telecom provider 1112 to forward the call to the hotel's main phone number, which is received at the cloud PBX server 120 and passed down to the appropriate onsite PBX server 104. Forwarding the call to the hotel by the mobile phone corresponds to step 1016 of FIG. 10.

The onsite PBX server 104 then recognizes the incoming call based on its caller ID information and connects the incoming call to the appropriate in-room phone 108 that was already answered by the user. This action corresponds to step 910 of FIG. 9. The user is now connected to the incoming caller and may use the in-room phone 108 to have a conversation.

FIG. 11 illustrates another example where the user chooses to answer an incoming call on the mobile phone 124. Interactions 1120, 1122, 1124 each correspond directly to the above-described interactions 1102, 1104, and 1106, respectively. The difference with example starts when the user answers the call on the mobile phone 124. When this occurs, the hotel application 610 sends a notification 1110 that the call is answered to the onsite PBX server 104. This notification 1110 corresponds to step 1012 of FIG. 10.

In response, the onsite PBX server 104 sends a stop ringing command 1128 to the in-room phone, which corresponds to step 914 of FIG. 9. (i.e., the onsite PBX server 104 disconnects the incoming call it had previously generated at step 908 of FIG. 9)

The incoming call is therefore answered and connected 1130 to the user's mobile phone 124.

After the user has checked out of the hotel 102*a*, the onsite PBX server 104 sends a notification 1132 to the hotel application 610 running on the mobile phone 124 to deactivate the custom incoming call rule (performed by the hotel app. 610 at step 1020 in FIG. 1020).

The hybrid PBX system 100 according to the embodiment of FIG. 1 has both an onsite PBX server 104 physically located at the hotel 102*a* and a cloud PBX server 120, which may be physically located anywhere because it is accessed via the Internet 104. The hybrid PBX system 100 takes all the information and data that is not real time and gives the hotel administrators the option to place that data in the cloud. Advantages of doing so include automated backups and central storage of databases, feature sets, voice mail messages, call accounting data, configuration information, etc. Furthermore, extension-to-extension (i.e., in-room phone 108*a* to in-room phone 108*a*) calls at the hotel 102*a* are fully handled by the onsite PBX server 104. Because the on-site PBX server 104 is located onsite, delay and other latency problems from sending voice calls via the Internet 104 are avoided.

The hybrid PBX system 100 therefore solves a problem with a cloud-only based PBX (i.e., a fully hosted PBX) which is delays on voice calls. Voice is a true real time issue and it is very dissatisfying to users to have latency and delays on voice data. For instance, 100 ms delay may cause echoes and 500 ms may result in collisions. Other timing issues in addition to latency in voice calls are also encountered in a fully cloud-based PBX system. For example, the timing of the hotel's PMS interface may not work when communicating with a remote server due to significant delays. Most hotels still have onsite PMS to handle back office and guest registrations etc. These onsite PMS do not support communication protocols and interfaces that allow for large delays that may be encountered when communicating with cloud based servers on the Internet. Because the hybrid PBX system 100 according to the embodiment of FIG. 1 includes an onsite PBX server 104, these problems may be avoided.

Furthermore, may hotels do not have the proper IP network to handle a fully hosted solution for phones, but they still want cloud features and benefits. To support analog phones 108, a hotel 102*a* may install analog to gateway ATA analog termination adaptors. For example, a gateway with 24 analog ports converting to SIP to IP. However, if trying to deploy a fully cloud-based PBX, since all calls go via the Internet 104, the bandwidth requirements from the hotel out to the Internet are significant. Compression may be considered and utilized if necessary to reduce the bandwidth requirements, but the compression itself adds greatly to the latency problems. Delay, jitter, chop, drop outs, etc. are all effects that experienced in a compressed audio stream such as G.729 (8 kbit/sec compressed) versus a standard G.711 (pulse code modulation (PCM), uncompressed 64 kbit/sec).

With the hybrid PBX system 100 of FIG. 1, in-room phones 108 can be analog or digital and no high level of compression is required to reduce Internet 104 bandwidth because room to room 112 calls are handled by the onsite PBX server 104. In the embodiment of FIG. 1, when a guest picks up an in-room phone 108, the dial tone is provided by the onsite PBX server 104, and any hotel calls made by the guest via an in-room phone 108 to another phone at the hotel are also handled fully by the onsite PBX server 104. No call data is needed to be send via the Internet 104.

In the embodiment of FIG. 1, voice mail is stored in cloud on storage media 146 at the cloud PBX server 120 as backup in case the onsite PBX server 104 fails and to offer unified messaging across multiple different properties hotel properties 102. But voice mail is also stored locally in the storage media 136 of the onsite PBX server 104 so that it is ready to be played back locally and will still be available if the hotel's 102*a* connection to the Internet 106 is overloaded or unavailable when the guests attempts to playback voicemails. For example, when working away from the hotel, a user can go to a voice mail portal website (e.g., offered by cloud PBX server 120) and then can play voice mail over speaker, which would be coming from the copy stored in the storage media 146 of cloud PBX server 120. Storing voice mail in only one of onsite or cloud PBX server 104, 120 rather than both is also an option in other embodiments.

In the embodiment of FIG. 1, basic call accounting records are stored on the onsite PBX server 104 while advanced call accounting records are stored on the cloud PBX server 120. The reason is to enable the cloud PBX server 120 to crunch the numbers for multiple hotel properties 102.

In the embodiment of FIG. 1, the onsite PBX server 104 directly interfaces with the hotel's on-site PMS 114 so problems with delay and latency experienced by a cloud-only solution are avoided. Both a serial and an IP interface between onsite PBX server 104 and the hotel's PMS 114 is available. Further, a Lotus Domino interface (server in the cloud) for interfacing with either the cloud PBX server 120 or the onsite PBX server 104 is also available so that charges can be posted to that server via Internet.

In the embodiment of FIG. 1, event logging is captured and stored in the cloud so that events such system failures and PMS interface problems are logged.

In the embodiment of FIG. 1, an auto-attendant telephone answering system may be provided on either or both of the onsite PBX server 104 and/or the cloud PBX server 120. For example, when an inbound call comes in, it hits the cloud auto attendant at the cloud PBX server 120 and never vectors to site unless requested. Integrated voice response (IVR) is included to allow the user's to say "one" instead of pressing the number "1". If the user presses or chooses to be transferred to reservations, the call is sent to the hotel reservations not to the local hotel 102a site. The hybrid PBX system 100 is also configured so that should the cloud PBX server 120 or onsite PBX server 104 fail, incoming calls will go directly to the hotel 102. For example, a call is placed to the hotel 102, the system sees a SIP trunk failure, then routes the call to hotel.

In the embodiment of FIG. 1, licensing information is stored in the storage media 146 at the cloud PBX server 120. In this way, when a hotel 102 adds a number of in-room phones 108, the hotel 102 needs to purchase licenses for those additional phones. Licenses can also be transferred to other sites 102. The onsite PBX server 104 periodically queries the cloud PBX server 120 and stores a local database of licensing in storage media 136y. If the onsite PBX server 104 is disconnected from the Internet 104 and cannot communicate with the cloud PBX server 120, the onsite PBX server 104 will work for a predetermined period of time such as 30 days. The hotel administrators can in to the cloud vendor to get a code to keep going for another 30, otherwise lacking a valid extension code and no current license for the hotel 102a retrievable from the cloud PBX server 120, the onsite PBX server 104 is configured to simply shut down.

In a fully hosted (cloud only) PBX solution, if the remote host fails, the hotel is dead in the water, even room to room calls will fail. However, in the embodiment of FIG. 1, should the cloud PBX server 120 or the hotel's 102a connection to the Internet fail, at least room 112 to room 112 calls via in-room phones 108 will still work, and outbound calls to external telephone numbers 116 may also continue to function assuming backup trunking 113 is installed.

In the embodiment of FIG. 1, the onsite PBX server 104 monitors the cloud PBX server 120 to detect problems. In the event the cloud PBX server 120 goes down or is otherwise unreachable, then the onsite PBX server 104 automatically starts routing calls to alternate PSTN path such as via backup trunking 113. The cloud PBX server 104 may also monitor and report problems detected with each of the onsite PBX servers 104 located at the various hotels 102.

Another advantage of the embodiment of FIG. 1 is that, because the onsite PBX server 104 handles room to room calls, not only is call quality better than typical hosted solution but also hotel saves money on bandwidth costs because local calls not routed externally. Yet another advantage of the embodiment of FIG. 1 is that the hotel still obtains many of the benefits of a fully cloud based system without the disadvantages inherent in those systems.

In an extension to the embodiment of FIG. 1, the onsite PBX server 104 can also be redundant onsite such that there are two onsite PBX servers 104. If one dies, the other automatically takes over. Cold redundancy can also be utilized to avoid wasted electricity and wear and tear on the backup onsite PBX server 104. In this embodiment, after the primary onsite PBX server 104 fails, hotel staff must physically switch the Ethernet cable from the dead onsite PBX server 104 to the cold redundant onsite PBX server and plug the cold redundant onsite PBX server in and turn on power. The cold redundant onsite PBX server then automatically boots up, sees Internet 104, reports that is the redundant onsite PBX server to the cloud PBX server 120, and downloads from the cloud PBX server 120 the current database and all other required information to begin operating as the onsite PBX server 104 for the hotel. Because most failures of an onsite PBX server 104 are power surge related such as lightning strikes etc., this embodiment preserves the viability of the backup onsite PBX server because it is not plugged in either network cable or power cable until it is actually required.

Although the invention has been described in connection with preferred embodiments, it should be understood that various modifications, additions and alterations may be made to the invention by one skilled in the art without departing from the spirit and scope of the invention as defined in the appended claims. For example, in another configuration of the invention, one or more of the various functions of the onsite PBX server 104 and the cloud PBX server 120 may be implemented as an external device such as a another computer having its own processor(s), network interface(s), storage medium/media, and other hardware necessary components.

In another modification example, rather than activating all custom call rules for a particular user exactly at check-in and exactly at checkout by the user (step 208 of FIG. 2), some or all of the custom rules for a particular user may be designed by either the user of the hotel as permanent. For example, certain VIP guests may wish to make setting 304 of FIG. 3 permanent even when the guest is not currently checked in to the hotel. Alternatively, some custom rules such as setting 304 of FIG. 3 for a particular guest may be activated a first predetermined duration before the guest is scheduled to arrive and a second predetermined duration after the guest as checked out.

In another modification example, despite the many advantages of a hybrid PBX system including both onsite and cloud PBX servers 104, 120 such as illustrated in FIG. 1, many of the above described features such as custom and dynamically activated incoming and outgoing call rules for currently checked in users may also be implemented in either a fully onsite PBX solution or a fully cloud (i.e., hosted) PBX solution. For example, in other embodiments of the invention, one of the onsite PBX server 104 or the cloud PBX server 120 may be omitted from the system 100 to thereby form either a fully hosted PBX solution or an onsite-only PBX solution, respectively.

In the above description, the exemplary user indication of "guest" is utilized to refer to users as it common for customers of a hospitality establishment to be referred to as guests. However, it is not a requirement that users must be customers of the hospitality establishment and the term "guest" in this description includes other users such as current guests in the hotel, people who are attending a conference or meeting in the hotel, staff members at the hotel, or any other person or user who may need or want to access a network service over a computer network at the hospitality establishment. Future guests that have reservations, potential future guests that don't yet have reservations, and other users may also be enabled to setup and benefit from custom incoming and outgoing call rules in a similar manner. For example, a demonstration of the technology may be available in a hotel lobby guest area and all users would be able to try out the system 100. Additionally, it is not necessary that the users bring their own mobile phone 124. In another configuration, one or more of the mobile phones 124 may be provided to the user by the hotel. It should also be noted that although portable phones that are easily carried are anticipated by the inventors as being particularly useful as the mobile phone 124, it is not a strict requirement that the mobile phone 124 be easily carried. Other larger devices capable of making phone calls such as phones integrated with computers or other electronic equipment capable of being moved may also act as mobile phone 124 in conjunction with the invention. Different mobile phone 124 communication standards such as GSM, CDMA, analog etc. may also be utilized in conjunction with the invention.

Although the invention has been described as being utilized at a hotel for illustration purposes, the present invention is equally applicable to any hospitality related location or service wishing to better complement user's mobile phones including but not limited to hotels, motels, resorts, hospitals, apartment/townhouse complexes, restaurants, retirement centers, cruise ships, busses, airlines, airports, shopping centers, passenger trains, libraries, coffee shops, hotspots, etc. Additionally, the invention is applicable to facilities where a PBX is required outside of the hospitality industry including home and corporate usages in addition to the above described hospitality examples.

In an exemplary embodiment of the invention, a PBX system co-operates with and complements the mobile phones of users. Custom incoming and outgoing call rules are dynamically activated for users when the users begin utilizing a facility having at least one phone number and a number of internal phones. A custom rule dynamically activated for a current user causes outgoing calls made from an internal phone used by the user to have a caller ID phone number of the user's personal mobile phone rather than the facility's phone number. Another custom rule dynamically activated for a current user causes incoming calls made to the facility's phone number that have a source caller ID phone number matching a phone number in the user's mobile phone address book to be automatically forwarded directly to an internal phone currently utilized by the user. A user may also install an application on their mobile phone, and another custom rule causes incoming calls at the user's mobile phone to be twinned while the user is at the facility so that both the user's mobile phone and an internal phone currently used by the user ring. The user may thereby choose on which to answer the call.

The various separate configurations, elements, features, embodiment, and modules of the invention described above may be integrated or combined. One or more processors operating pursuant to instructions stored on a tangible, non-transitory computer-readable medium to perform the above-described functions. Examples of the tangible, non-transitory computer-readable medium include optical media (e.g., CD-ROM, DVD discs), magnetic media (e.g., hard drives, diskettes), and other electronically readable media such as flash storage devices and memory devices (e.g., RAM, ROM). The computer-readable medium may be local to the computer executing the instructions, or may be remote to this computer such as when coupled to the computer via a computer network such as the Internet 104. The one or more processors may be included in a general-purpose or specific-purpose computer that becomes a special purpose machine performing described functions as a result of executing the instructions. In another example, rather than being software modules executed by one or more processors, the various modules and described functionality such as actions performed by the onsite PBX server 104 and cloud PBX server 120 may be implemented as hardware modules configured to perform the above-described functions. Functions of single modules and devices as described may be separated into multiple units, or the functions of multiple modules and devices may be combined into a single unit. Unless otherwise specified, features described may be implemented in hardware or software according to different design requirements. In addition to a dedicated physical computing device, the word "server" may also mean a service daemon on a single computer, virtual computer, or shared physical computer or computers, for example. Additionally, all combinations and permutations of the above described features and configurations may be utilized in conjunction with the invention.

What is claimed is:

1. A hospitality phone system for processing incoming telephone calls, the hospitality phone system comprising:
   a storage device storing a default incoming call rule specifying a default destination to which incoming telephone calls to a hospitality establishment are to be forwarded; and
   one or more processors configured to:
       store a custom incoming call rule in the storage device, the custom incoming call rule is based at least in part on: a user specifying a source telephone number and the user selecting whether to allow twin incoming calls to both a custom destination and a mobile phone associated with the source telephone number;
       track when the user is checked in to the hospitality establishment and activating the custom incoming call rule only when the user is checked in to the hospitality establishment;
       receive a first incoming telephone call during a period of time when the user is checked in to the hospitality establishment;
       compare a source caller identification (ID) number of the first incoming telephone call with the source telephone number specified in the custom incoming call rule;
       when the source caller ID number of the first incoming telephone call matches the source telephone number specified in the custom incoming call rule, forward the first incoming telephone call to the custom destination at the hospitality establishment different than the default destination based at least in part on the stored custom incoming call rule;
       receive a second incoming telephone call during a period of time when the user is not checked in to the hospitality establishment, the second incoming telephone call also having a source caller ID number matching the source telephone number specified in the custom incoming call rule; and forward the second incoming telephone call to the default destination according to the default incoming call rule because the custom incoming call rule is not active when the user is not checked in to the hospitality establishment.

2. The system of claim 1, wherein the default destination is a phone extension corresponding to the front desk of the hospitality establishment.

3. The system of claim 1, wherein the default destination is a phone extension corresponding to an auto-attendant answering service for the hospitality establishment.

4. The system of claim 1, wherein the custom destination is a predetermined phone extension at the hospitality establishment.

5. The system of claim 1, wherein the custom destination is a phone extension corresponding to a concierge desk at the hospitality establishment.

6. The system of claim 1, wherein the one or more processors are further configured to allow the user to create the custom incoming call rule further specifying the custom destination at the hospitality establishment.

7. The system of claim 1, wherein the one or more processors are further configured to, when the source caller ID number of the first incoming telephone call matches the source telephone number in the custom incoming call rule:
look up a particular guest room of the hospitality establishment that is currently registered to the user who created the custom incoming call rule according to a user identifier of the user; and
change the source caller (ID) number to the particular guest room when forwarding the first incoming telephone call to the custom destination at the hospitality establishment.

8. The system of claim 1, wherein the one or more processors are further configured to, when the source caller ID number of the first incoming telephone call matches the source telephone number in the custom incoming call rule:
look up a particular guest room of the hospitality establishment that is currently registered to the user who created the custom incoming call rule according to a user identifier of the user; and
forward the first incoming telephone call to the custom destination being a phone extension corresponding to the particular guest room currently registered to the user.

9. The system of claim 8, wherein the one or more processors are further configured to look up in a property management system (PMS) of the hospitality establishment the particular guest room that is currently registered to the user.

10. The system of claim 8, wherein the one or more processors are further configured to:
allow the user to enable a voice mail service for incoming telephone calls to the phone extension corresponding to the particular guest room currently registered to the user; and
automatically copy the outgoing message for the voice mail service from a pre-existing outgoing message on an external voice mail server at an external phone number provided by the user.

11. The system of claim 1, wherein the one or more processors are further configured to:
allow the user to create the custom incoming call rule further specifying a destination telephone number provided by the user; and
when the source caller ID number of the first incoming telephone call matches the source telephone number in the custom incoming call rule, simultaneously forward the first incoming telephone call to both the custom destination at the hospitality establishment and to the destination phone number provided by the user.

12. The system of claim 1, further comprising:
allowing the user to create the custom incoming call rule at a central server that is accessible by a plurality of hospitality establishments; and
downloading the custom incoming call rule by a controller at a particular one of the hospitality establishments.

13. A system for processing outgoing telephone calls in a hospitality phone system, the hospitality phone system comprising:
a storage device storing a default outgoing call rule specifying a default telephone number to employ as a source caller identification (ID) for outgoing calls made from guest rooms at a hospitality establishment; and
one or more processors configured to:
create and storing a custom outgoing call rule, the custom outgoing call rule at least specifying a custom telephone number provided by a user;
track when the user is checked in to the hospitality establishment and activating the custom outgoing call rule only when the user is checked in to one of a plurality of different guest rooms at the hospitality establishment;
receive a first outgoing telephone call during a period of time when the user is checked in to a particular guest room of the hospitality establishment;
determine that the first outgoing telephone call was made from a phone extension in the particular guest room that is currently registered to the user according to a user identifier of the user;
transmit the custom telephone number specified in the custom outgoing call rule as the source caller ID when forwarding the first outgoing telephone call to an outside phone network;
receive a second outgoing telephone call during a period of time when the user is not checked in to the hospitality establishment, the second outgoing telephone call made from the phone extension in the particular gust room; and
transmit the default telephone number specified in the default outgoing call rule as the source caller ID when forwarding the second outgoing telephone call to the outside phone network because the custom outgoing call rule is not active when the user is not checked in to the hospitality establishment.

14. The system of claim 13, wherein the one or more processors are further configured to look up in a property management system (PMS) of the hospitality establishment the particular guest room that is currently registered to the user.

15. The system of claim 13, wherein the one or more processors are further configured to:
allow the user to create the custom outgoing call rule at a central server that is accessible by a plurality of hospitality establishments; and
download the custom outgoing call rule by a controller at a particular one of the hospitality establishments.

* * * * *